US008548559B2

(12) United States Patent
Hodgson et al.

(10) Patent No.: US 8,548,559 B2
(45) Date of Patent: Oct. 1, 2013

(54) METHOD AND APPARATUS FOR COMPUTER-ASSISTED FEMORAL HEAD RESURFACING

(75) Inventors: Antony Hodgson, Vancouver (CA); Kevin Bryant Inkpen, Vancouver (CA); Carolyn Anglin, Calgary (CA)

(73) Assignee: Orthosoft, Inc., Montreal (CA)

( * ) Notice: Subject to any disclaimer, the term of this patent is extended or adjusted under 35 U.S.C. 154(b) by 990 days.

(21) Appl. No.: 11/917,507

(22) PCT Filed: Jun. 19, 2006

(86) PCT No.: PCT/CA2006/001008
§ 371 (c)(1),
(2), (4) Date: Dec. 14, 2007

(87) PCT Pub. No.: WO2006/133573
PCT Pub. Date: Dec. 21, 2006

(65) Prior Publication Data
US 2008/0214960 A1    Sep. 4, 2008

Related U.S. Application Data

(60) Provisional application No. 60/691,164, filed on Jun. 17, 2005.

(51) Int. Cl.
*A61B 5/05* (2006.01)
(52) U.S. Cl.
USPC .............. 600/407; 606/130; 378/20; 378/205
(58) Field of Classification Search
USPC ........... 600/587, 595, 407; 623/13.12, 18.11, 623/20.14, 20.35–23.47, 902; 378/20, 205; 606/130
See application file for complete search history.

(56) References Cited

U.S. PATENT DOCUMENTS 5,772,594 A *  6/1998  Barrick .................. 600/407
6,450,978 B1 *  9/2002  Brosseau et al. ........... 600/595
(Continued)

FOREIGN PATENT DOCUMENTS

| JP | 2003-153913 | 5/2003 |
| JP | 2004-237100 | 8/2004 |

(Continued)

OTHER PUBLICATIONS

Amstutz H.C., Beaule P.E., Dorey F.J., Le Duff M.J., Campbell P.A., Gruen T.A., *Metal-on-metal hybrid surface arthroplasty: two to six-year follow-up study*, J Bone Joint Surg Am, Jan. 2004; 86-A(1):28-39.

(Continued)

*Primary Examiner* — Rene Towa
(74) *Attorney, Agent, or Firm* — Norton Rose Fulbright Canada LLP

(57) ABSTRACT

A method for locating a guide wire axis on a femoral neck comprises the steps of tracking a position and orientation of a femur; registering a frame of reference with respect to the position and orientation of the femur from a first registration probe mounted onto the femur in a predetermined configuration, the frame of reference having preoperative planned data pertaining to the femoral neck; digitizing femoral neck data with respect to the position and orientation of the femur from a second registration probe positioned onto the femoral neck at desired orientations; calculating a position and orientation of the guide wire axis with respect to the position and orientation of the femur as a function of the preoperative planned data and the femoral neck data.

18 Claims, 17 Drawing Sheets

(56) References Cited

U.S. PATENT DOCUMENTS

| | | | |
|---|---|---|---|
| 2003/0069591 | A1 | 4/2003 | Carson et al. |
| 2003/0208122 | A1* | 11/2003 | Melkent et al. ............... 600/426 |
| 2004/0082849 | A1* | 4/2004 | Schweikard et al. ......... 600/424 |
| 2004/0087852 | A1 | 5/2004 | Chen et al. |
| 2004/0143340 | A1* | 7/2004 | Tuma et al. ................ 623/22.12 |
| 2004/0153062 | A1 | 8/2004 | McGinley et al. |
| 2004/0167654 | A1 | 8/2004 | Grimm et al. |
| 2004/0254584 | A1* | 12/2004 | Sarin et al. .................... 606/102 |
| 2005/0021037 | A1 | 1/2005 | McCombs et al. |

FOREIGN PATENT DOCUMENTS

| | | |
|---|---|---|
| JP | 2004-237101 | 8/2004 |
| JP | 2005-525868 | 9/2005 |
| WO | 2004/019792 | 3/2004 |
| WO | 2004/107993 | 12/2004 |

OTHER PUBLICATIONS

Beaule P.E., Amstutz H.C., Le Duff M., Dorey F., *Surface arthroplasty for osteonecrosis of the hip: hemiresurfacing versus metal-on-metal hybrid resurfacing*, J Arthroplasty, Dec. 2004; 19(8 Suppl 3):54-8.

Callaghan J.J., O'rourke M.R., Saleh K.J., *Why knees fail: lessons learned*, J Arthroplasty, Jun. 2004; 19(4 Suppl 1):31-4.

Chandler H.P., Reineck F.T., Wixson R.L., McCarthy J.C., *Total hip replacement in patients younger than thirty years old. A five-year follow-up study*, J Bone Joint Surg Am, Dec. 1981; 63(9):1426-34.

Daniel J., Pynsent P.B., McMinn D.J., *Metal-on-metal resurfacing of the hip in patients under the age of 55 years with osteoarthritis*, J Bone Joint Surg Br, Mar. 2004; 86(2):177-84.

Dorr L.D., *Comparison of primary total hip replacements performed with a standard incision or a mini-incision*, J Bone Joint Surg Am, Mar. 2005; 87-A(3):675.

Duffy G.P., Prpa B., Rowland C.M., Berry D.J., *Primary uncemented Harris-Galante acetabular components in patients 50 years old or younger: results at 10 to 12 years*, Clin Orthop Relat Res, Oct. 2004; (427):157-61.

Joshi A.B., Porter M.L., Trail I.A., Hunt L.P., Murphy J.C., Hardinge K., *Long-term results of Charnley low-friction arthroplasty in young patients*, J Bone Joint Surg Br, Jul. 1993; 75(4):616-23.

McMinn D., Treacy R., Lin K., Pynsent P., *Metal on metal surface replacement of the hip. Experience of the McMinn prothesis*, Clin Orthop Relat Res, Aug. 1996; (329 Suppl):S89-98.

Mont M.A., Rajadhyaksha A.D., Hungerford D.S., *Outcomes of limited femoral resurfacing arthroplasty compared with total hip arthroplasty for osteonecrosis of the femoral head*, J Arthroplasty, Dec. 2001; 16(8 Suppl 1):134-9.

Mont M., Bezweda H., Thomas C., Etienne G., *The results of metal on metal resurfacing hip arthroplasty: learning curve stratification of results*, American Academy of Orthopaedic Surgeons, Washington DC, Feb. 22-27, 2005.

Shekman M., Masri B.A., Greidanus N.V., Garbuz D.S., Duncan C.P., Anglin C., Hodgson A.J., Inkpen K.B., *Variability of femoral positioning in hip resurfacing arthroplasty*, 51st Annual Meeting of the Orthopaedic Research Society, Washington, DC, Feb. 20-23, 2005.

Sugano N., Nishii T., Kahahodo K., Sasama T., Sato Y., Tamura S., Sakai K.T., Haraguchi K., Nishihara S., Ozono K., Yodenobu K., Yoshikawa H. and Ochi T., *Combined acetabular and femoral navigation for resurfacing total hip arthroplasty*, Computer Assisted Radiology and Surgery, San Francisco, 226-230, 2000.

Treacy R.B., McBryde C.W., Pynsent P.B., *Birmingham hip resurfacing arthroplasty. A minimum follow-up of five years*, J Bone Joint Surg Br, Feb. 2005; 87(2):167-70.

Wacek G. and Boyle D., *Techniques of computer assisted surgery applied to metal on metal hip resurfacing procedures*, Galway-Mayo Inst. of Technology (IRL), Computer Assisted Radiology and Surgery, 2003.

Zambelli P.Y., Brégand C.H., Dewarrat S.T., Marti G.S., Baur C.H. and Leyvarz P.F., *Planning and navigation solution in resurfacing hip surgery—A way to reduce the surgical approach*, Computer-Assisted Orthopaedic Surgery, Marbella, Spain, 2003.

\* cited by examiner

METHOD AND APPARATUS FOR COMPUTER-ASSISTED FEMORAL HEAD RESURFACING

CROSS-REFERENCE TO RELATED APPLICATION

The present patent application is a national-phase entry of International Application No. PCT/CA2006/001008, filed Jun. 19, 2006, and claims priority on U.S. Provisional Application No. 60/691,164, filed Jun. 17, 2005.

BACKGROUND OF THE INVENTION

1. Field of the Invention

The present invention relates to the field of computer assisted surgery (CAS), in particular procedures for implantation and revision of artificial joint and bone components. Particular focus of the invention is on intraoperative registration of a bone, transfer of preoperatively planned geometry to bone, and intraoperative characterization of the bone. The present invention is particularly adapted for computer assisted Femoral Head Resurfacing (FHR).

2. Background Art

With an aging population, bone and joint deterioration due to a number of different diseases—most notably arthritis, is an increasingly common occurrence. A common procedure—total hip replacement (total hip arthroplasty—THA)—has been successfully used in older patients with predictable and durable results. Some of the initial issues in regards to implant mobility and wear and tear have been overcome with the advent of new generation of implants and materials. However, the results in younger and more active patients have been less predictable, especially where older reconstructive techniques and materials such as bone cement have been used. In THA procedures involving younger patients a significant amount of problems have been observed in relation to the articular bearing wear and component loosening [*Primary uncemented Harris-Galante acetabular components in patients 50 years old or younger: results at 10 to 12 years*, by Duffy G. P., Prpa B., Rowland C. M., and Berry D. J., Clin Orthop Relat Res, 2004 October; *Why knees fail: lessons learned*, by Callaghan J. J., O'rourke M. R. and Saleh K. J., J Arthroplasty, 2004 June; *Total hip replacement in patients younger than thirty years old. A five-year follow-up study*, J Bone Joint Surg Am, 1981 December; *Comparison of primary total hip replacements performed with a standard incision or a mini-incision*, by Dorr, L. D., J Bone Joint Surg Am, 2005 March; and *Long-term results of Charnley low-friction arthroplasty in young patients*, by Joshi A. B., Porter M. L., Trail I. A., Hunt L. P., Murphy J. C., Hardinge K., J Bone Joint Surg Br, 1993 July]. While some of the issues have been overcome, there is still a significant concern in relation to the long term prognosis for active patients whose remaining lifespan may be in excess of 150 years.

A particular concern for younger patients is the desire to "gain time" and delay entry to the medullary canal—the inside cavity of the bone which contains the bone marrow. THA procedures require a long stem to be inserted into the medullary canal, which can trigger fat emboli during surgery, potentially leading to pulmonary occlusion, and can begin a process of bone resorption and degeneration which can limit the overall life of the implant. An alternative procedure to THA, available in modern orthopedic surgery, is Femoral Head Resurfacing (FHR). FHR has been particularly helpful for younger patients afflicted with osteoarthritis or avascular necrosis of the femoral head [*Metal-on-metal hybrid surface arthroplasty: two to six-year follow-up study*, by Amstutz H. C., Beaule P. E., Dorey F. J., Le Duff M. J., Campbell P. A., and Gruen T. A., J Bone Joint Surg Am, 2004 January; *Surface arthroplasty for osteonecrosis of the hip: hemiresurfacing versus metal-on-metal hybrid resurfacing*, by Beaule P. E., Amstutz H. C., Le Duff M., Dorey F., J Arthroplasty, 2004 December; and *Metal-on-metal resurfacing of the hip in patients under the age of 55 years with osteoarthritis*, by Daniel J., Pynsent P. B., McMinn D. J., J Bone Joint Surg Br, 2004 March]. In FHR method, the acetabular cavity of the innominate is lined with a new socket similar to the THA. However, unlike THA which requires cutting off superior component of the femur at the neck point, FHR requires only that the femoral head is reamed such that a new artificial femoral head cup can be secured over it. FHR technique not only preserves femoral head bone stock, but, in comparison to THA, also more closely approximates normal hip kinematics, joint stability and proprioception, while minimizing the potential for post-operative leg length discrepancy and stress shielding of the proximal femur [*Birmingham hip resurfacing arthroplasty. A minimum follow-up of five years*, by Treacy R. B., McBryde C. W. and Pynsent P. B. J Bone Joint Surg Br, 2005 February; *Metal on metal surface replacement of the hip. Experience of the McMinn prothesis*, by McMinn D., Treacy R., Lin K. and Pynsent P., Clin Orthop Relat Res, 1996 August; and *Surface arthroplasty for osteonecrosis of the hip: hemiresurfacing versus metal-on-metal hybrid resurfacing*, by Beaule P. E., Amstutz H. C., Le Duff M., Dorey F., J Arthroplasty, 2004 December]. Furthermore, it has been suggested that due to extremely low rates of articular bearing wear in metal on metal hip resurfacing arthroplasty, this technique may permit the patient to return to a greater level of activity and sport than other reconstructive options [*Surface arthroplasty for osteonecrosis of the hip: hemiresurfacing versus metal-on-metal hybrid resurfacing*, by Beaule P. E., Amstutz H. C., Le Duff M., Dorey F., J Arthroplasty, 2004 December]. Indeed, even though younger patients place high activity demands on these implants, early clinical results are very good with multiple authors reporting 2 to 5 year implant success of 194-198% [*Metal-on-metal hybrid surface arthroplasty: two to six-year follow-up study*, by Amstutz H. C., Beaule P. E., Dorey F. J., Le Duff M. J., Campbell P. A., and Gruen T. A., J Bone Joint Surg Am, 2004 January; *Metal-on-metal resurfacing of the hip in patients under the age of 55 years with osteoarthritis*, by Daniel J., Pynsent P. B., McMinn D. J., J Bone Joint Surg Br, 2004 March; and *Birmingham hip resurfacing arthroplasty. A minimum follow-up of five years*, by Treacy R. B., McBryde C. W. and Pynsent P. B. J Bone Joint Surg Br, 2005 February].

Despite the attractive clinical results and success, however, there continues to be a number of complications and potential concerns with the surgical technique that are unique to FHR. In comparison to total hip arthroplasty, the surgical technique is more complex and demands higher degree of precision from the surgeon. In order to adequately visualize the femoral head and neck to properly orient and place the new cup, surgeon must use a wide exposure of the hip which results in longer incision and potentially longer healing times. The instrumentation for femoral head preparation is based entirely upon the placement of a femoral head and neck guide pin. Pin placement is a time-consuming process in the operating room and despite the surgeon's efforts to centre the pin using intraoperative guides and calipers, the surgical technique can be unreliable [*Variability of femoral positioning in hip resurfacing arthroplasty*, 51st Annual Meeting of the Orthopaedic, by Shekhman M., Masri B. A., Greidanus N. V., Garbuz D. S., Duncan C. P., Anglin C., Hodgson A. J., and Inkpen K. B., Research Society, Washington, D.C., Feb. 20-23, 2005] and may result in sub-optimal component placement or notching. Notching—unplanned cortical bone violation—occurs where the bone is reamed or cut in a location where it will not be covered by the new femoral head cup. Notching is of particular concern as it has been demonstrated to increase the risk of postoperative femoral neck fracture [*Metal-on-metal resurfacing of the hip in patients under the age of 55 years with osteoarthritis*, by Daniel J., Pynsent P. B., McMinn D. J., J Bone Joint Surg Br, 2004 March; and *Metal on metal surface replacement of the hip. Experience of the McMinn prothesis*, by McMinn D., Treacy R., Lin K. and Pynsent P., Clin Orthop Relat Res, 1996 August]. In addition, malposition of the guide pin may result in oversizing the femoral head component, which may then necessitate excessive removal of acetabular bone stock for acetabular component placement. Malposition of the femoral component may also compromise the hip's range of motion and patient satisfaction with the procedure. Failure to pay attention to these nuances may explain some of the unique complications of resurfacing arthroplasty which include post-operative femoral neck fracture requiring revision surgery, implant loosening, and avascular necrosis of the femoral head, which may result in symptoms of pain or femoral head collapse and loosening of the resurfacing component [*Surface arthroplasty for osteonecrosis of the hip: hemiresurfacing versus metal-on-metal hybrid resurfacing*, by Beaule P. E., Amstutz H. C., Le Duff M., Dorey F., J Arthroplasty, 2004 December]. These highly technical aspects of the procedure are evident in improvement in the accuracy of component placement and reductions in the rates of femoral neck notching, fracture and revision with increasing numbers of resurfacing procedures performed [*Outcomes of limited femoral resurfacing arthroplasty compared with total hip arthroplasty for osteonecrosis of the femoral head*, by Mont M. A., Rajadhyaksha A. D. and Hungerford D. S. J Arthroplasty, 2001 December; and *The results of metal on metal resurfacing hip arthroplasty: learning curve stratification of results*, by Mont M., Bezweda H., Thomas C., Etienne G., American Academy of Orthopaedic Surgeons, Washington D.C., Feb. 22-27, 2005].

Existing methods to improve femoral head/neck pin placement and instrumentation of the femoral head have largely involved preoperative planning, complex kinematic modelling, and radiographic calculations. In addition, a number of mechanical apparatus such as jigs, calipers, and femoral neck gauges have been developed to help guide the surgeon's pin placement intraoperatively. Despite the refinement of these methods, there continues to be tremendous variability in final guide-pin placement and femoral component placement [*Variability of femoral positioning in hip resurfacing arthroplasty*, 51st Annual Meeting of the Orthopaedic, by Shekhman M., Masri B. A., Greidanus N. V., Garbuz D. S., Duncan C. P., Anglin C., Hodgson A. J., and Inkpen K. B., Research Society, Washington, D.C., Feb. 20-23, 2005] among both novice and experienced hip surgeons.

SUMMARY OF INVENTION

Therefore, it is an object of the present invention to provide a method and apparatuses addressing issues associated with the prior art.

Therefore, in accordance with the present invention, there is provided a method for locating a guide wire axis on a femoral neck, comprising the steps of: tracking a position and orientation of a femur; registering a frame of reference with respect to the position and orientation of the femur from a first registration probe mounted onto the femur in a predetermined configuration, the frame of reference having preoperative planned data pertaining to the femoral neck; digitizing femoral neck data with respect to the position and orientation of the femur from a second registration probe positioned onto the femoral neck at desired orientations; calculating a position and orientation of the guide wire axis with respect to the position and orientation of the femur as a function of the preoperative planned data and the femoral neck data.

Further in accordance with the present invention, there is provided a caliper tool for digitizing a midline of a bone element, comprising: a trackable reference secured to the caliper tool; a handle portion; a pair of jaws connected to the handle portion and displaceable with respect to one another, the jaws each having a contact surface being adapted to abut concurrently opposite portions of a bone in such a way that a midline of the bone is calculable from the position of the contact surfaces of the jaws with respect to the trackable reference.

Proposed herein is a method of computer-assisted navigation in conjunction with novel apparatus that may be used to optimally prepare the femoral head and place the guide pin and component. This method is an improvement in outcomes of resurfacing by decreasing complication rates (reduced femoral neck notching/fracture rate and avascular necrosis), improving component placement and hip range of motion/kinematics, decreasing length of time in the operating room, allowing surgeons to use the smallest size femoral head component safely possible for each patient (and therefore minimize unnecessary acetabular bone removal for acetabular instrumentation), and creating opportunities to perform resurfacing through less invasive surgical incisions. The approach may be applied to other bones such as the humerus where appropriate reference points may be identified on preoperative radiographs.

In accordance with one aspect of the invention, there is provided a registration tool for registering the position of a bone in space during surgery. The registration tool may have a flat planar first surface, a flat planar second surface oriented at a selected angle to the first surface, with the first surface adapted to contact at least two preselected anatomical features of the bone and the second surface adapted to contact at least three preselected anatomical features of the bone, thereby constraining the registration tool in at least 5 degrees of freedom relative to the bone, and means for sensing and recording the position of the registration tool in space.

The bone may be a femur and the preselected anatomical features may include a superior aspect of the femoral head, superior aspect of the greater trochanter, posterior aspect of the femoral head, posterior aspect of the greater trochanter, posterior aspect of the lesser trochanter, and supramedial aspect of the femoral head. More specifically, the first surface may contact superior aspects of the femoral head and the greater trochanter, and the second surface may contact posterior aspects of the femoral head, greater trochanter, and lesser trochanter.

In accordance with another aspect of the invention, the registration tool may further comprise a third flat planar surface adapted to contact a sixth preselected anatomical feature of the bone, thereby constraining the sixth degree of freedom of the probe relative to the bone. The bone may be a femur and the additional anatomical feature may be the superomedial aspect of the femoral head.

One experienced in the art will appreciate that the registration tool may be constructed with one or more contact surfaces, each designed to make contact with at least one point on the bone. Five such contact points are necessary to position an axis at a desired orientation relative to a reference frame on the bone, and a sixth point is necessary to position the axis at a desired position relative to the reference frame. The contact points need not be acquired simultaneously but may be staggered in time, so long as the positions of the contact surfaces are measured relative to the bone at times when they are in contact with the bone.

In accordance with another aspect of the invention, there is provided a measuring device for characterizing an anatomical feature during surgery, the measuring device having a first surface, a second surface substantially parallel to the first surface, a means to vary the distance between the first and second surfaces within a preselected range and means for sensing and recording the position of a preselected geometric form having a preselected position relative to the first and second surfaces. The measuring device may be a caliper tool, and the first and second surfaces may each be an edge having a length and a negligible width. The anatomical feature may be a femoral neck and the preselected geometric form may be a midline parallel and equidistant to the first and second edges.

Sensing and recording means comprising these embodiments may comprise a computer navigation tracking system.

In accordance with another aspect of the invention, there is provided a method of locating an axis passing through the centre of the femoral neck during surgery, the method comprising the steps of:

selecting a planned implant axis in an anteroposterior plane radiograph of the femur having a varus/valgus angle relative to the at least two anatomical features visible in the anteroposterior radiograph, which may be the superior aspects of the greater trochanter and femoral head;

selecting an anteversion angle of the desired axis, as viewed in a mediolateral radiograph of the femur, relative to the at least three additional anatomical features visible in the mediolateral plane radiograph which may be the posterior aspects of the greater trochanter, femoral head, and lesser trochanter;

sensing the position of the femur during surgery using a registration tool having a first surface that contacts at least two anatomical features, and a second surface that contacts at least three anatomical features of the femur;

calculating an approximate frontal plane relative to the at least three additional anatomical features contacting the second surface of the registration tool calculating a superior reference plane relative to the approximate frontal plane and the at least two anatomical features contacting the first surface of the registration tool;

calculating the orientation of the planned implant axis relative to the approximate frontal plane and the superior reference plane using the varus/valgus angle and the anteversion angle;

recording a set of approximately proximodistal midlines through the femoral neck lying approximately parallel to the approximate frontal plane using a measuring device such as a caliper tool;

recording an approximately anteroposterior midline through the femoral neck at approximately its narrowest point, and lying approximately normal to the approximate frontal plane, using the caliper tool;

calculating a first projection plane normal to the desired axis and passing through the intersection of the anteroposterior midline and the approximate frontal plane;

calculating a femoral neck centre by projecting the proximodistal midlines and the anteroposterior midline into the first projection plane and averaging the intersection points of each of the proximodistal midlines and the anteroposterior midline as projected into the first projection plane;

calculating a second projection plane normal to the approximate frontal plane and at the varus/valgus angle and passing through the femoral neck centre, and;

calculating the final implant axis as the least squares best fit line to the intersection points of the proximodistal midlines and the second projection plane.

The method may alternately substitute selection of the anteversion angle on a mediolateral radiograph with a preselected anteversion angle.

In accordance with another aspect of the invention, there is provided a method of locating an axis passing through the centre of the femoral neck during surgery, the method comprising the steps of:

selecting a planned implant axis in an anteroposterior plane radiograph of the femur having a varus/valgus angle relative to at least two anatomical features visible in the anteroposterior plane radiograph, which may be the superior aspects of the greater trochanter and femoral head;

sensing the position of the femur during surgery using a registration tool having a first surface that contacts at least two anatomical features, and a second surface that contacts at least three anatomical features of the femur calculating an approximate frontal plane relative to the at least three additional anatomical features contacting the second surface of the registration tool calculating a superior reference plane relative to the approximate frontal plane and the at least two anatomical features contacting the first surface of the registration tool;

recording a set of approximately proximodistal midlines through the femoral neck lying approximately parallel to the approximate frontal plane using a measuring device such as a caliper tool;

recording an approximately anteroposterior midline through the femoral neck at approximately its narrowest point, and lying approximately normal to the approximate frontal plane, using the caliper tool;

calculating an approximate midplane of the femoral neck passing as closely as possible through the proximodistal midlines;

calculating a femoral neck centre which is the intersection of the anteroposterior midline and the approximate midplane;

calculating a second projection plane normal to the approximate frontal plane and at the varus/valgus angle and passing through the femoral neck centre, and;

calculating the final implant axis as the least squares best fit line to the intersection points of the proximodistal midlines and the second projection plane.

In accordance with another aspect of the invention, there is provided a method of locating an axis passing through the centre of the femoral neck, the method comprising:

selecting a planned implant axis and a planned implant point on the planned implant axis in an anteroposterior plane radiograph of the femur having a varus/valgus angle and a position relative to at least three anatomical features visible in the frontal plane radiograph, which may be the superior aspects of the greater trochanter and femoral head, and the superomedial aspect of the femoral head;

sensing the position of the femur during surgery using a registration tool having a first surface and a third surface that contact the at least three anatomical features, which may be the superior aspects of the greater trochanter and femoral head, and the superomedial aspect of the femoral head; and a second surface that contacts at least three additional anatomical features of the femur which may be the posterior aspects of the greater trochanter, lesser trochanter, and femoral head;

calculating an approximate frontal plane relative to the at least three additional anatomical features contacting the second surface of the registration tool;

calculating a superior reference plane relative to the first surface of the registration tool;

recording a set of approximately proximodistal midlines through the femoral neck lying approximately parallel to the approximate frontal plane using a measuring device such as a caliper tool;

calculating an approximate midplane of the femoral neck passing as closely as possible through the proximodistal midlines;

calculating a second projection plane normal to the approximate frontal plane and at the varus/valgus angle and passing through the femoral neck centre, and;

calculating the final implant axis as the least squares best fit line to the intersection points of the proximodistal midlines and the second projection plane.

The methods described above may further comprise sensing and recording a set of potential notching points on the femoral neck, calculating a radius which is the minimum cylindrical radius about the final implant axis that encloses the set of potential notching points; comparing the radius to a user selected radius, and if the radius is greater than the user selected radius and it is geometrically possible, translating the final implant axis the minimum amount required to make the user selected radius about the translated final implant axis enclose the set of potential notching points. The method may further comprise rotating the final implant axis to make the user selected radius about the final implant axis enclose the set of potential notching points Other aspects and features of the present invention will become apparent to those ordinarily skilled in the art upon review of the following description of the specific preferred embodiments of the invention in conjunction with the accompanying figures.

BRIEF DESCRIPTION OF DRAWINGS

A preferred embodiment of the present invention will now be described with reference to the accompanying drawings in which.

DESCRIPTION OF THE PREFERRED EMBODIMENTS

Figure 1:
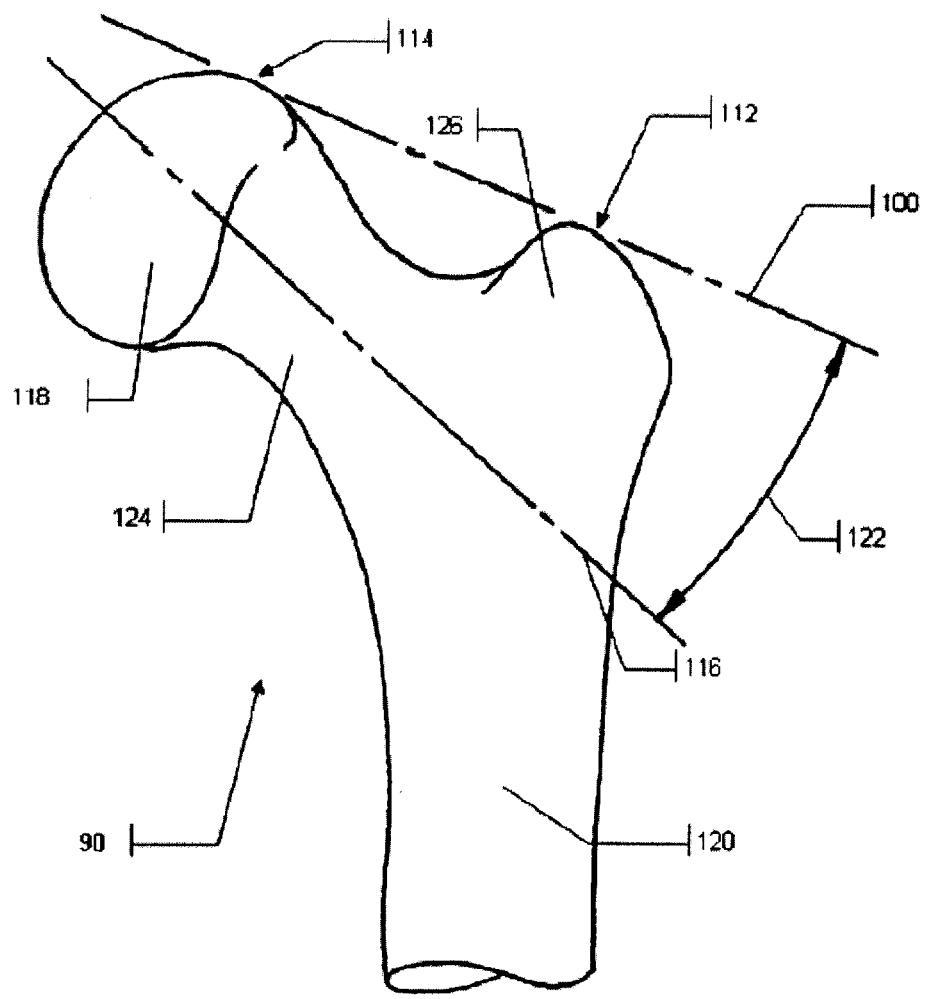
FIG. 1 shows the preoperative planning based on a frontal plane radiograph.

The invention and its presently preferred embodiment will be better understood by reference to the detailed disclosure below and/or the accompanying drawings.

As used herein, anteroposterior is a direction relative to the body and can be used to describe the direction from which a radiograph is made. The radiograph may be obtained by positioning the x-ray line of sight substantially normal to the frontal plane of the body.

As used herein, varus/valgus angle refers to the angle between the implant axis and the natural axis of the femoral neck as viewed in the anteroposterior direction. If the implant axis is directed above the neck axis as it moves laterally, the implant is said to be in varus.

As used herein, mediolateral is a direction relative to the body and can be used to describe the direction from which a radiograph is made. The radiograph may be obtained by positioning the x-ray line of sight substantially normal to the sagittal plane of the body.

As used herein, proximodistal is a direction relative to the body and can be used to describe the direction from which a radiograph is made. The radiograph may be obtained by positioning the x-ray line of sight substantially normal to the transverse plane of the body.

As used herein ante/retroversion angle refers to the angle between the frontal plane and a feature (such as the implant axis) having medial portions and more lateral portions further from the midplane of the body. If the feature is rotated causing its medial portions to move further anterior to the frontal plane than its more lateral portions, the angle of rotation is said to be anteversion.

As used herein, navigation system is a combination of a computer, a computer display, sensor device connected to the computer, and a plurality of markers the spatial position of which can be determined by the said navigation system. The sensor and markers can employ any type of tracking method as may be known in the art, for example emitter/detector systems based on optical or other technologies.

As used herein, a caliper tool is a device having two substantially parallel edges, a means of changing the distance between two said edges, and a means to determine a line parallel and equidistant to the two said edges. In contrast, calipers known in the prior art are commonly used in machine shops to measure the diameters (either internal or external) of circular objects; in such instruments, one of the said edges is able to slide along a ruled handle with a high degree of friction to enable it to stay in place when released by the user, and the distance between the edges is displayed. In the system described here, the midline between the two edges would most commonly be determined by calibrating the positions of the edges relative to optical markers mounted on the caliper tool, and then optically tracking the markers as the caliper is opened or closed. In such cases, the optical tracking system would be the navigation system used in the procedure.

As used herein, a digitizing probe is a device known in the art and used in conjunction with the navigation system to record spatial position of a point in physical contact with the probe.

As used herein, a trackable drill guide (TDG) is a device consisting of a tubular guide through which a drill is inserted connected to a rigid body to which is mounted some form of trackable hardware, most commonly a plurality of optical markers which may be tracked by the navigation system. The guide is calibrated such that the position and orientation of the tubular guide is known relative to the tracked hardware and the system can then report the drill axis and TDG tip location to the computer.

As used herein, a search algorithm is a computational technique used to solve a minimization problem which is typically expressed as a cost function of several parameters (many such search algorithms are well-known in the literature and include such techniques as the simplex algorithm, conjugate gradient approaches, Gauss-Newton approaches or genetic algorithms).

With reference to FIG. 1, in accordance with an embodiment, the preoperative surgical plan is shown generally at 90, as presented on an anteroposterior radiograph. A femoral head 118 of a femur 120 is connected to a greater trochanter 126 via a femoral neck 124. In the preferred embodiment, a superior reference plane 100 which is normal to the plane of the AP radiograph (and is therefore defined by a line on the radiograph), is made on the anteroposterior radiograph and passes through the superior aspect 112 of the greater trochanter 126 and the superior aspect 114 of the femoral head 118. A planned implant axis 116 is determined by the surgeon at the desired varus/valgus angle 122 between superior reference plane 100 and planned implant axis 116.

Figure 2:
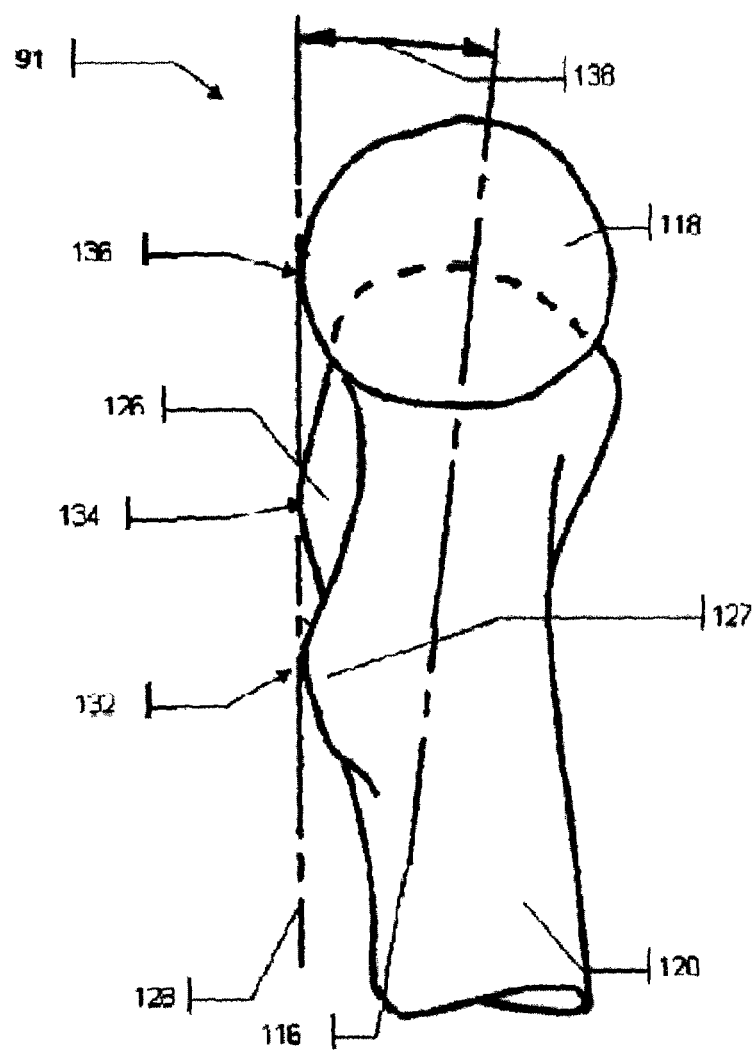
FIG. 2 shows the preoperative planning based on a sagittal plane radiograph.

With reference to FIG. 2, in accordance with an embodiment, the preoperative surgical plan is shown generally at 91, as presented on a mediolateral radiograph. This view is shown looking laterally out from the midline of the body with the proximal femoral head 118 of the femur 120 partially obscuring the greater trochanter 126. In this preferred embodiment, a posterior reference plane 128 which is normal to the mediolateral radiograph may be made on the preoperative to surgical plan passing through a posterior aspect 132 of the lesser trochanter 127, a posterior aspect 134 of the greater trochanter 126, and a posterior aspect 136 of the femoral head 118. In practice, aspects 132, 134 may not be collinear with aspect 136, in which case second reference line 128 may be drawn to pass through aspect 136 and approximately midway between aspects 132 and 134. The planned implant axis 116 may be determined by the surgeon at the desired ante/retroversion angle 138 and generally follows an ante/retroversion angle of natural axis of the femoral neck. If a mediolateral radiograph is not available or if aspects 132, 134 are not very collinear with aspect 136, ante/retrovision angle 138 may be the surgeon's estimate, or a default value representing typical anatomy. Ante/retroversion angle 138 is optimized intraoperatively based on measurements taken directly on the femur 120 as described below.

Figure 3:
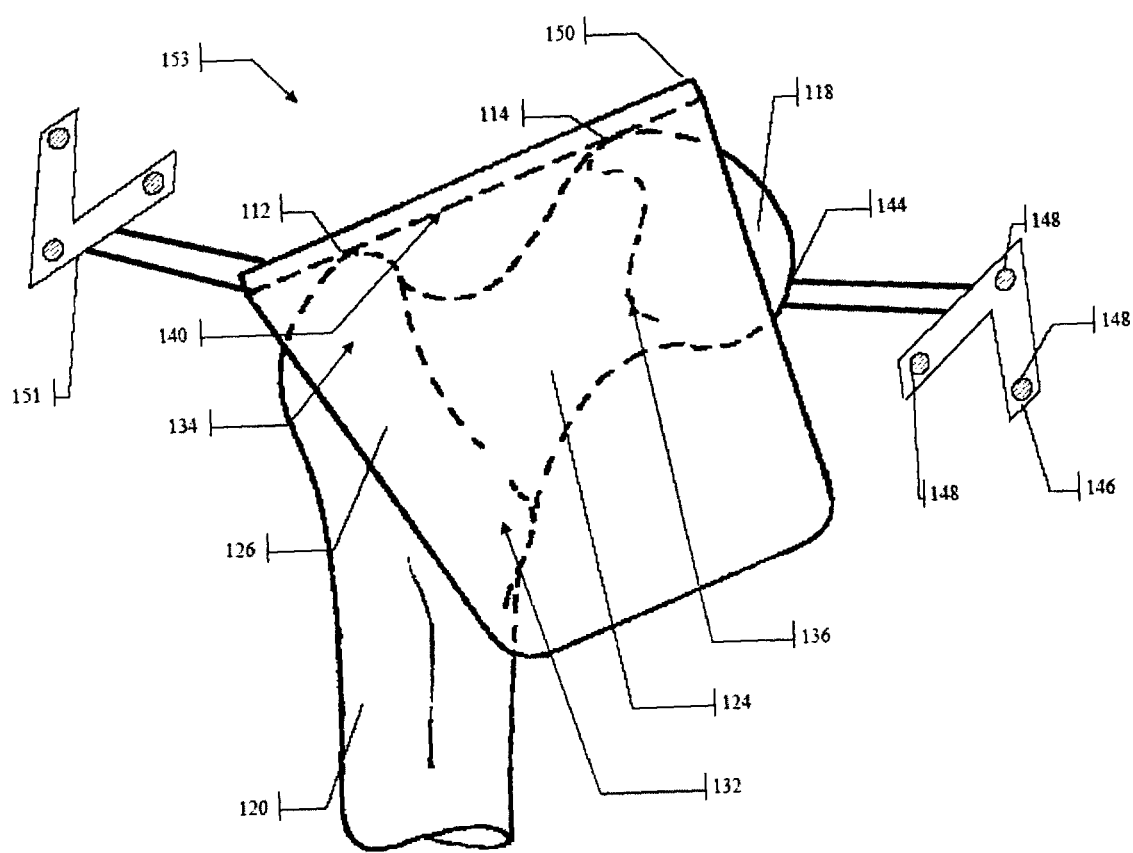
FIG. 3 shows the intraoperative positioning of the registration tool on the exposed femur, looking on the frontal plane.

With reference to FIG. 3, in accordance with an embodiment, a reference frame is shown generally at 146. The reference frame 146 contains markers 148, which may be tracked by the navigation system to determine absolute or relative position and orientation of the reference frame 146 in space. The reference frame 146 may attach to any exposed portion of the femur 120. In a preferred embodiment, the reference frame 146 is attached to the femoral head 118 at attachment points 144. Femoral neck 124 is shown for reference.

Figure 4:
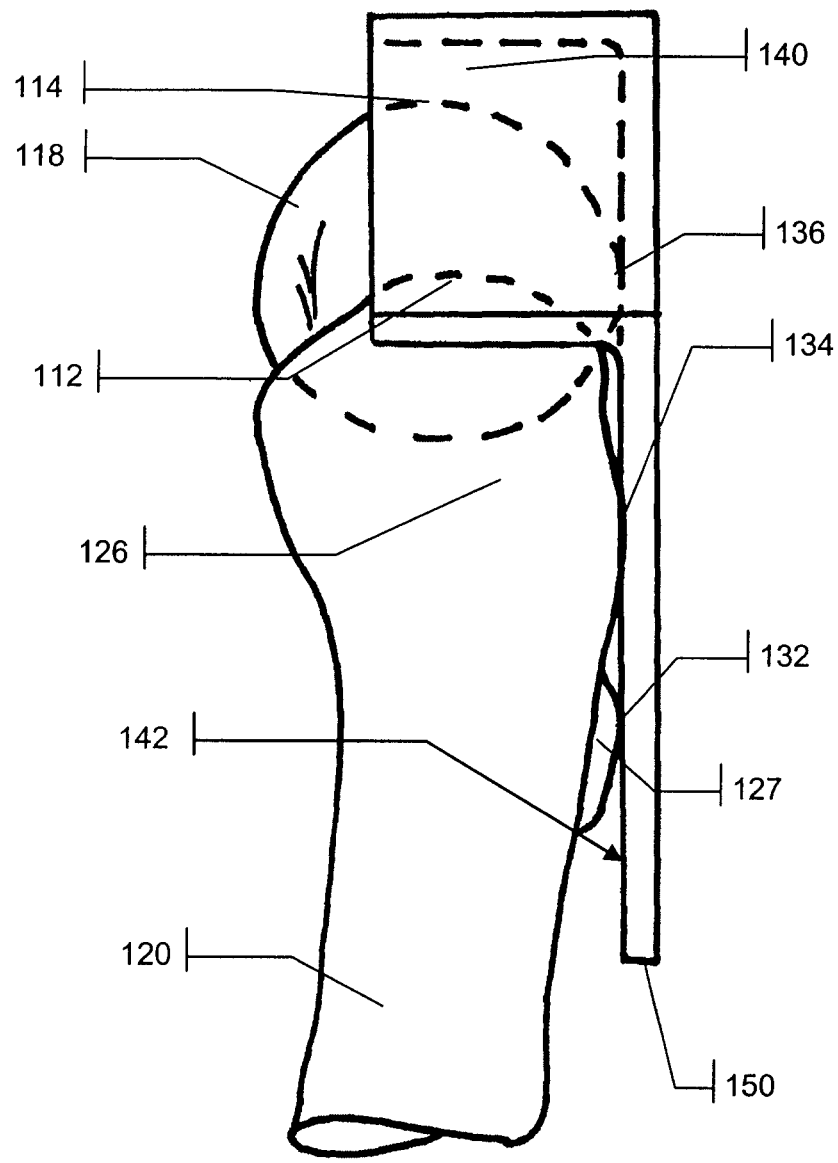
FIG. 4 shows the intraoperative positioning of the registration tool on the exposed femur, looking on the sagittal plane.

With reference to FIG. 3 and FIG. 4, an embodiment is shown generally at 153. In this preferred embodiment, the first registration tool 150 has a rigid planar first surface 140 which is substantially perpendicular to the rigid planar second surface 142. The surfaces may not be planar, however that implementation may be found to be convenient. The first registration tool 150 may have a set 151 of tracking markers attached to it such that its position and orientation in space may be tracked by a navigation system. In the preferred embodiment, the first surface 140 of the first registration tool 150 contacts the superior aspect 114 of the femoral head 118 and the superior aspect 112 of the greater trochanter 126. The second surface 142 contacts the posterior aspect 136 of the femoral head 118, the posterior aspect 134 of the greater trochanter 126, and the posterior aspect 132 of the lesser trochanter 127. When in contact at these five points, the first registration tool 150 is aligned with the superior 100 and posterior 128 reference planes from the preoperative surgical plans 90 and 91 as shown in FIGS. 1 and 2 and is constrained in five degrees of freedom relative to the femur 120, allowing orientations of features defined in the preoperative surgical plans 90 and 91 relative to superior 100 and posterior 128 reference planes to be defined relative to the femur 120 via frame of reference 146, which is tracked to provide a position and orientation of the femur and information related thereto.

Those skilled in the art will appreciate that registration tool 150 may be adapted to a wide variety of registration tasks involving different bones and different surgical procedures by selection of the form of the planar surfaces on the tool to suit reference features that can be identified in radiographs.

Figure 5:
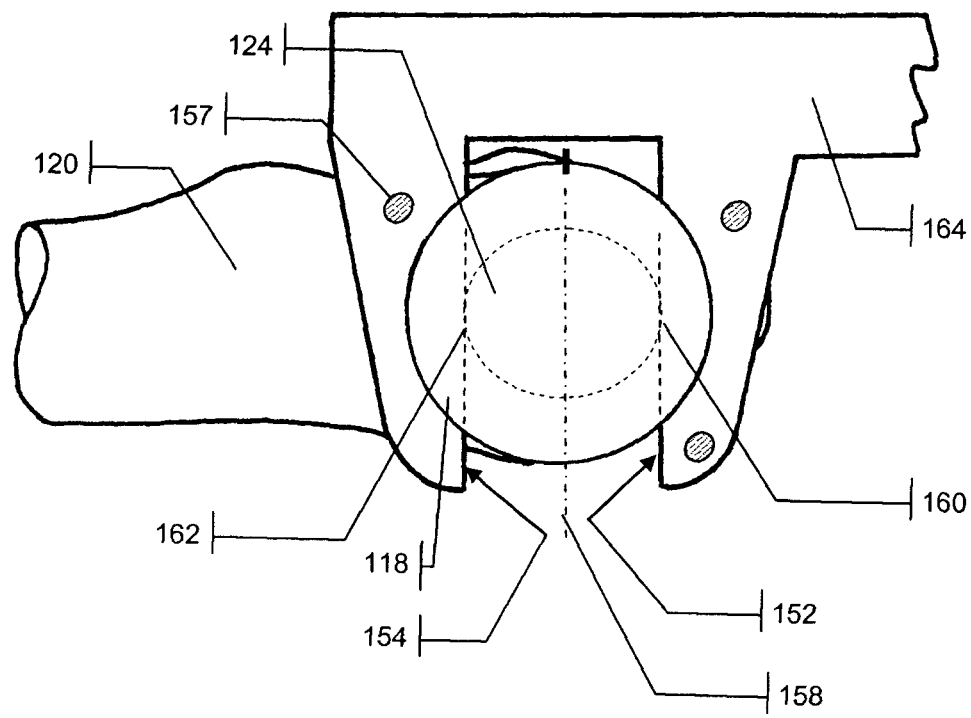
FIG. 5 shows the intraoperative neck center measurement using the caliper tool in the superior/inferior position.
Figure 6:
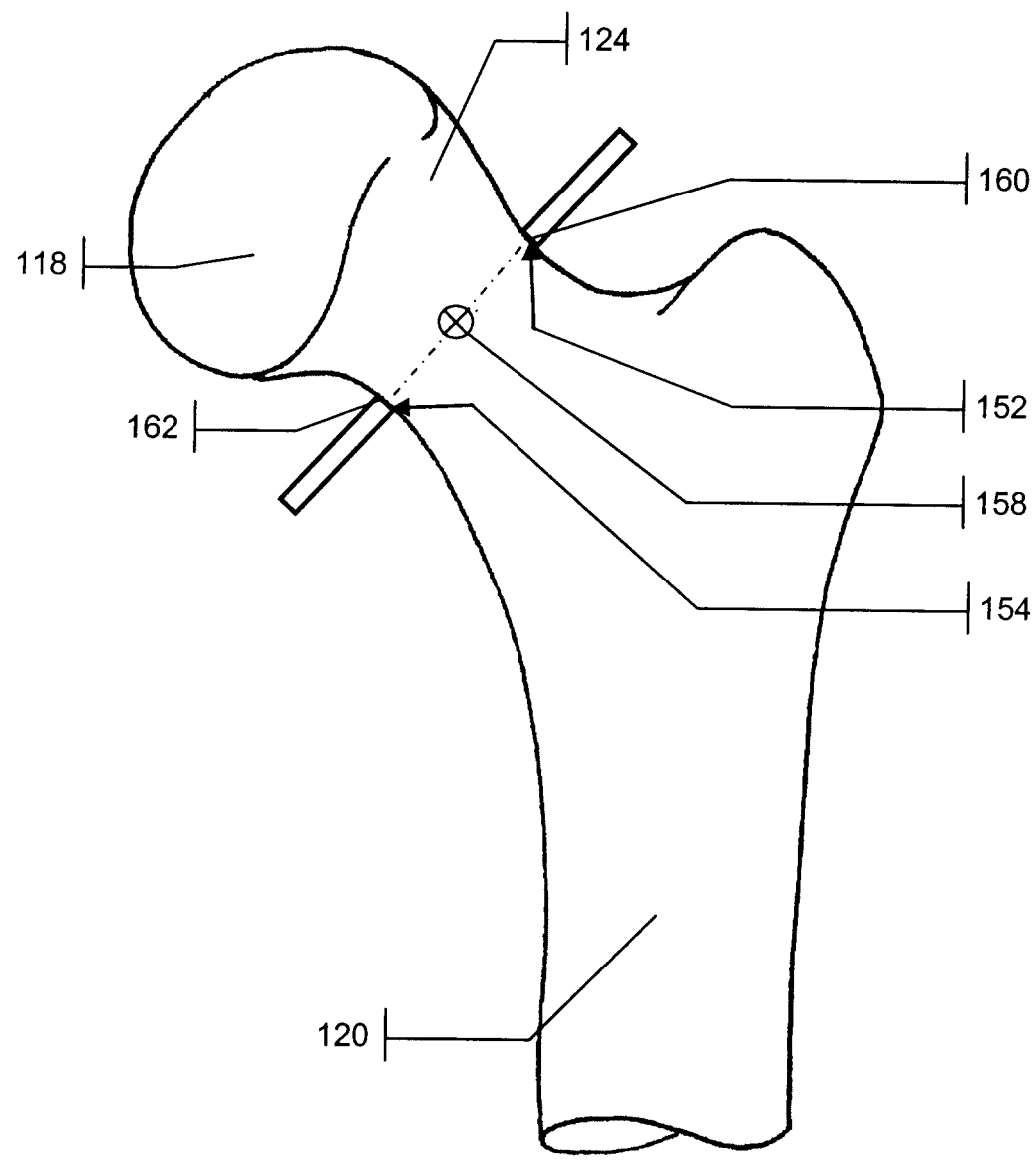
FIG. 6 shows the caliper measurement from FIG. 5, looking on the frontal plane.

As shown in FIG. 5 and FIG. 6, in accordance with an embodiment of the invention, the faces of the caliper tool 164 (i.e., the second caliper tool) may be closed such that a first jaw having a caliper face 152 (i.e., contact surface) contacts the superior aspect 160 and a second jaw having a caliper face 154 (i.e., contact surface) contacts the inferior aspect 162 of the narrowest section of the femoral neck 124 (as viewed in the frontal plane). Caliper tool 164 has a handle portion and emitters 153A and 155 mounted rigidly with respect to second caliper face 154 and emitter 157 mounted rigidly with respect to first caliper face 152. The positions in space of emitters 153A, 155, and 157 may be tracked by the navigation system relative to reference frame 146 as shown in FIG. 3. The predetermined geometry and calibration of caliper tool 164 defines the position of anteroposterior midline 158 parallel and equidistant to relative to first 152 and second 154 caliper faces. Therefore anteroposterior midline 158 passes approximately through the middle of the femoral neck 124 at its narrowest point and the position and orientation of anteroposterior midline 158 is defined relative to the femur 120 via reference frame 146. Those skilled in the art will appreciate that any geometric forms may be defined relative to first 152 and second 154 caliper faces and the geometric form may be selected to best characterize the anatomy of interest. Femoral head 118 is shown for reference.

Those skilled in the art will also appreciate that a variety of arrangements or three or more emitters may be used to define a geometric form specific to the distance between first 152 and second 154 caliper faces, provided not all emitters are mounted rigidly with respect to either first 152 or second 154 caliper face. For instance, as the jaws of the caliper tool 164 are displaceable relative to one another to adapt the caliper tool 164 to different dimensions of bones, it is contemplated to provide a mechanism in the handle portion, which mechanism would have the jaws move concurrently with respect to the handle portion. Therefore, with such a mechanism, the distances between each contact surface and a reference point on the handle would always be equal. The midline is aligned with this reference point in such a way that the caliper tool 164 needs only an initial calibration. Alternatively, two sets of trackable reference both trackable for position and orientation could be positioned on respective jaws of the caliper tool 164.

Figure 7:
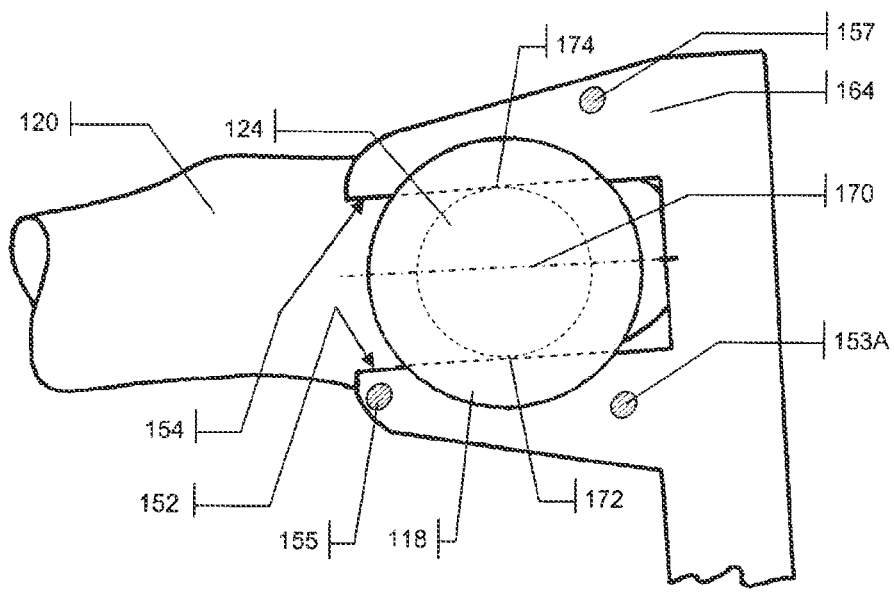
FIG. 7 shows the intraoperative neck center measurement using the caliper tool in the anterior/posterior position.
Figure 8:
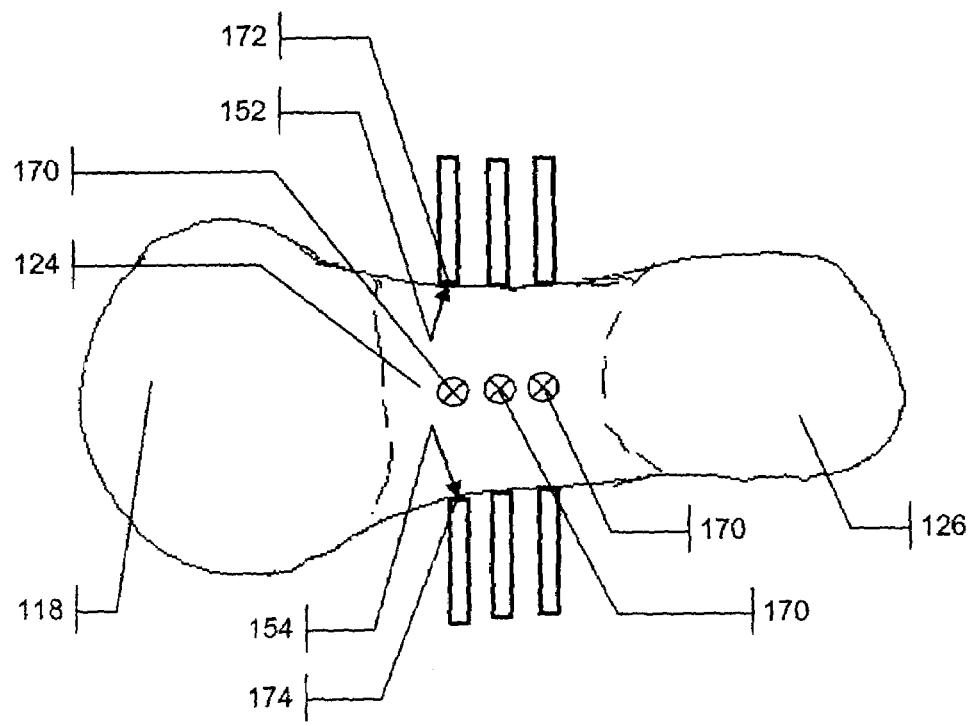
FIG. 8 shows the caliper measurement from FIG. 7, as seen looking on the transverse plane.

As shown in FIG. 7 and FIG. 8, in accordance with an embodiment of the invention, the faces of the caliper tool 164 may be closed such that the first caliper face 152 contacts an anterior aspect 172 and second caliper face 154 contacts an inferior aspect 174 of the femoral neck 124. In this preferred embodiment, at least 3 measurements may be taken at positions spread out along the femoral neck 124, resulting in a set of at least 3 substantially parallel proximodistal midlines 170 defined relative to the femur 120, using the caliper probe in the manner described above for FIG. 5.

Figure 9:
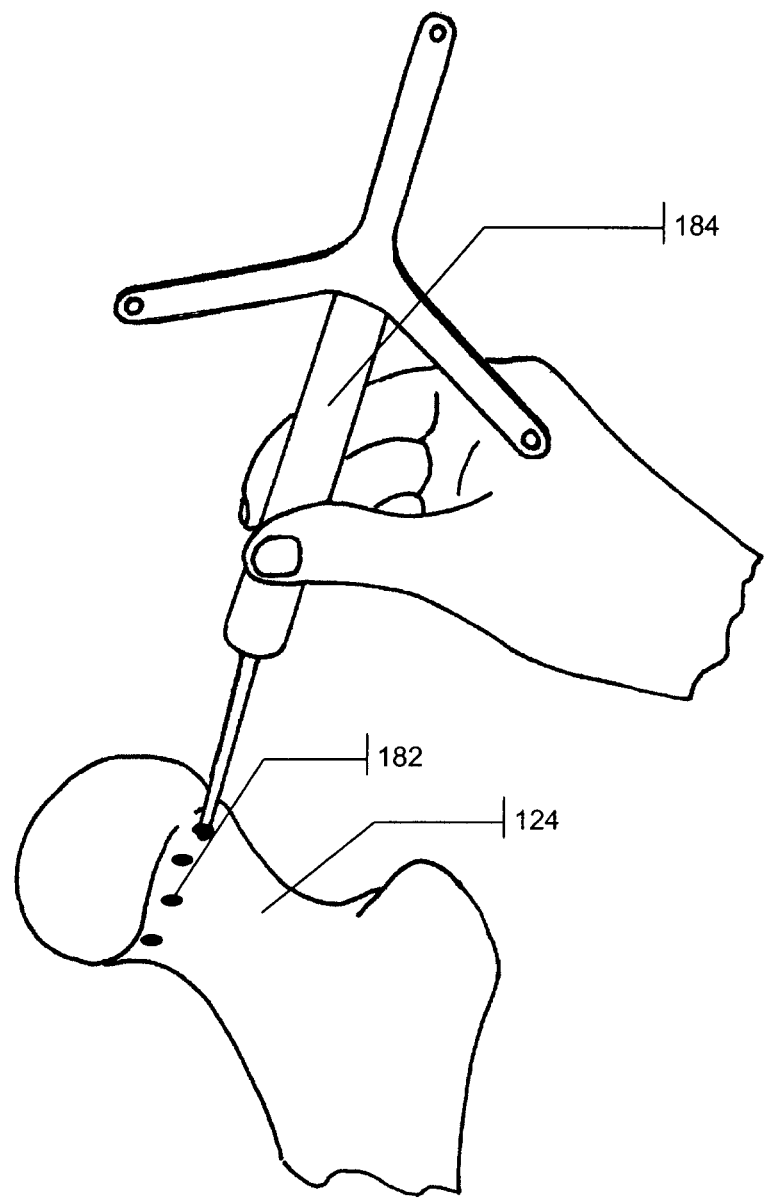
FIG. 9 shows the intraoperative operation of the digitizing probe.
Figure 10:
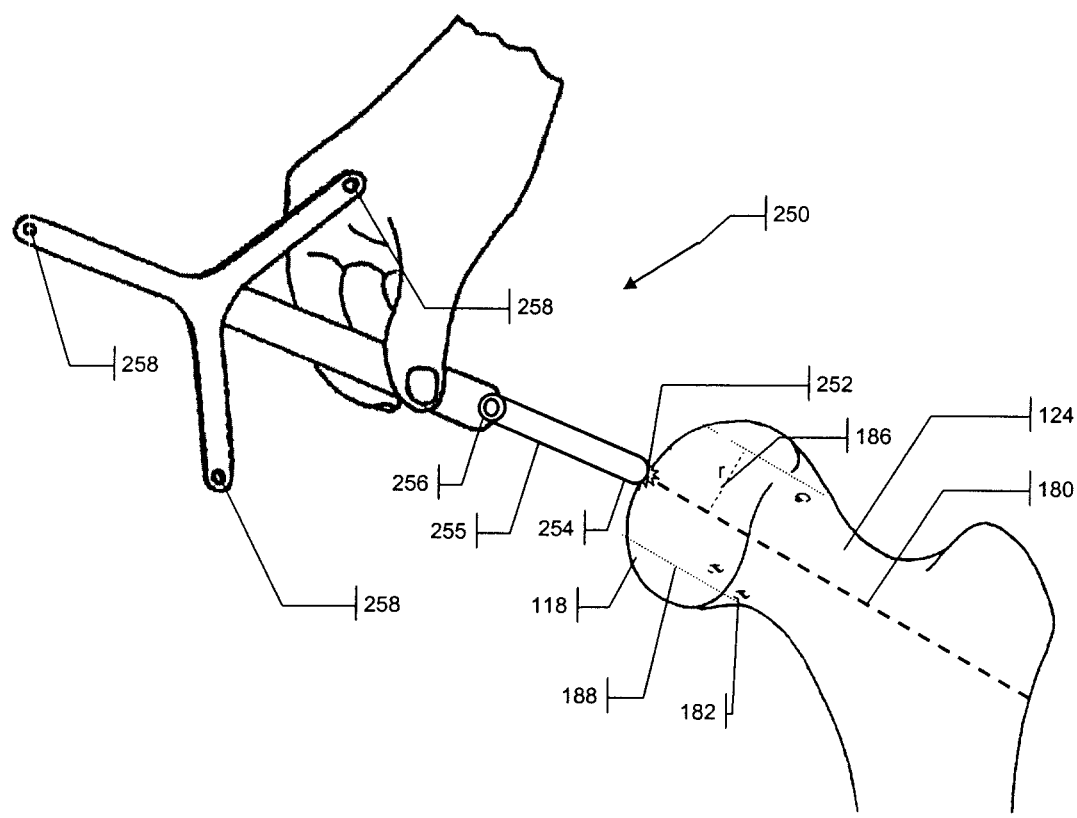
FIG. 10 shows the intraoperative operation of the tracked drill guide.

With references to FIG. 9 and FIG. 10, in accordance with an embodiment of the invention, the operation of a digitizing probe 184 is described. The position of the digitizing probe 184 is tracked by the navigation system. The probe may be used to record positions of the potential notching points 182 on the femoral neck 124. The minimum cylindrical radius 186 about the final implant axis 180 defines a cylinder which will enclose all of the potential notching points 182. Cylindrical reamer path 188 results when a reamer (of the typical type currently used in femoral head resurfacing procedures) of minimum cylindrical radius 186 is selected and guided along final implant axis 180 to resect the femoral head to receive the femoral head implant. Cylindrical reamer path 188 passes outside all potential notching points 182 and thereby leaves the femoral neck cortical bone intact at potential notching points 182, while allowing use of the minimum size femoral head implant.

As seen in FIG. 10, in accordance with an embodiment of the invention, the trackable drill guide 250 touches femoral head 118 at point 252. The trackable drill guide 250 may be aimed such that its angle coincides with the final implant axis 180. The position of the trackable drill guide 250 is tracked by the navigation system using a set of trackable markers 258. Trackable drill guide 250 has a rigid tubular section 255 of an inside diameter chosen to be a close sliding fit over the drill or pin desired to pass into the femur along axis 180. In use, tip 254 of rigid tubular section 255 is placed against the femur, and tail 256 of rigid tubular section 255 lies nearest the operator.

Figure 11:
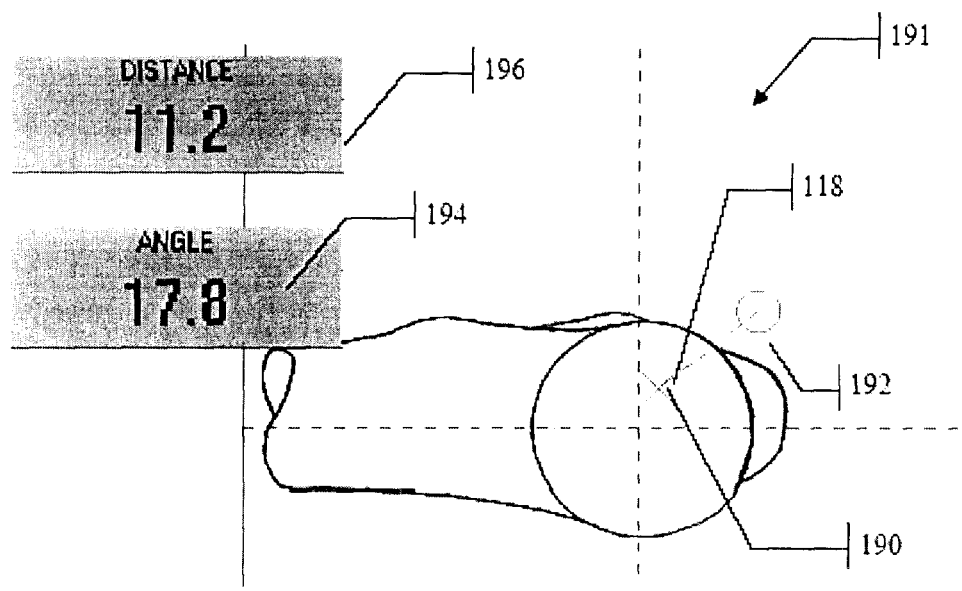
FIG. 11 shows the intraoperative operation of the tracked drill guide targeting system with the drill guide axis far off the calculated implant axis.
Figure 12:
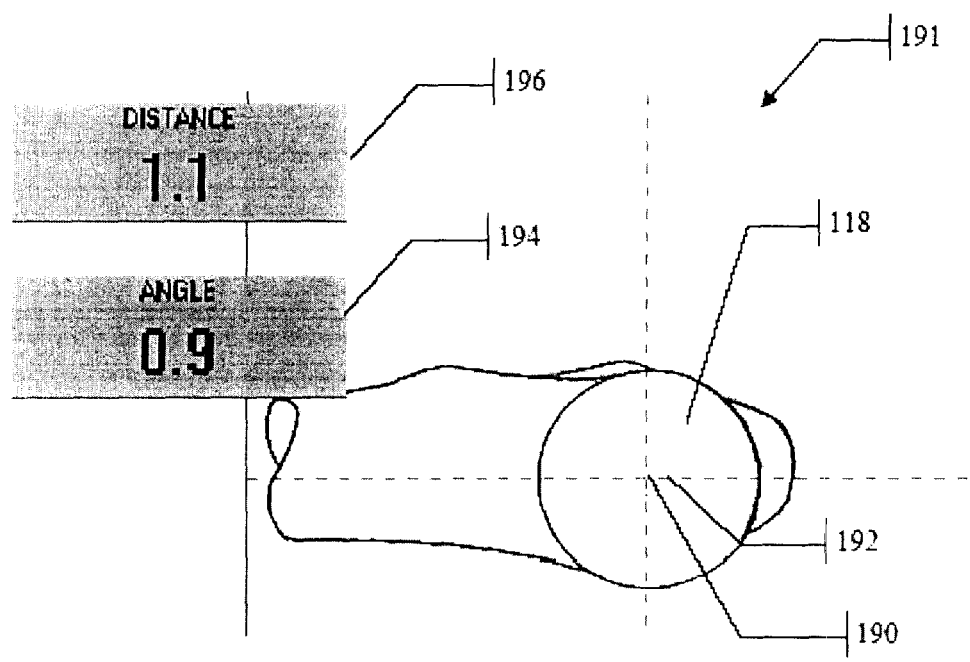
FIG. 12 shows the intraoperative operation of the tracked drill guide targeting system with the drill guide axis close to the calculated implant axis.

With references to FIG. 10, FIG. 11 and FIG. 12, in accordance with an embodiment of the invention, the positioning of a trackable drill guide 250 in accordance to the determined final implant axis 180 is described. In this preferred embodiment, a targeting screen 191 of a custom developed navigation system is shown. On the targeting screen 191, the distance of the tip 254 of the trackable drill guide 250 from the final implant axis 180 is shown numerically at 196 and visually at 190. The current angle of the trackable drill guide is indicated numerically at 194 and also by the visualized position of the tail 256 of the trackable drill guide 250 at 192. The numerical indicators 194, 196 and the visual indicators 190, 192 update as the position and orientation of the trackable drill guide 250 is adjusted. The trackable drill guide 250 is aligned with the final implant axis when the tip 254 position 190 and tail 256 position 192 coincide on the targeting screen 191 and the distance 194 and angle 196 displayed are within predetermined tolerance range about the final implant axis 180, as shown in FIG. 12. In one embodiment, in order to minimize the amount of attention which the surgeon must pay to the targeting screen, the target symbols 190, 192 may change colour and an audible alert sound when the position 196 and angulation 194 of the trackable drill guide 250 are within a predetermined tolerance range about the final implant axis 180.

The use of the trackable drill guide is optional and represents only one of the potential embodiments. In another potential embodiment, the drill itself may be similarly adapted and calibrated to report position information to the navigation system—such drills are commercially available.

Figure 13:
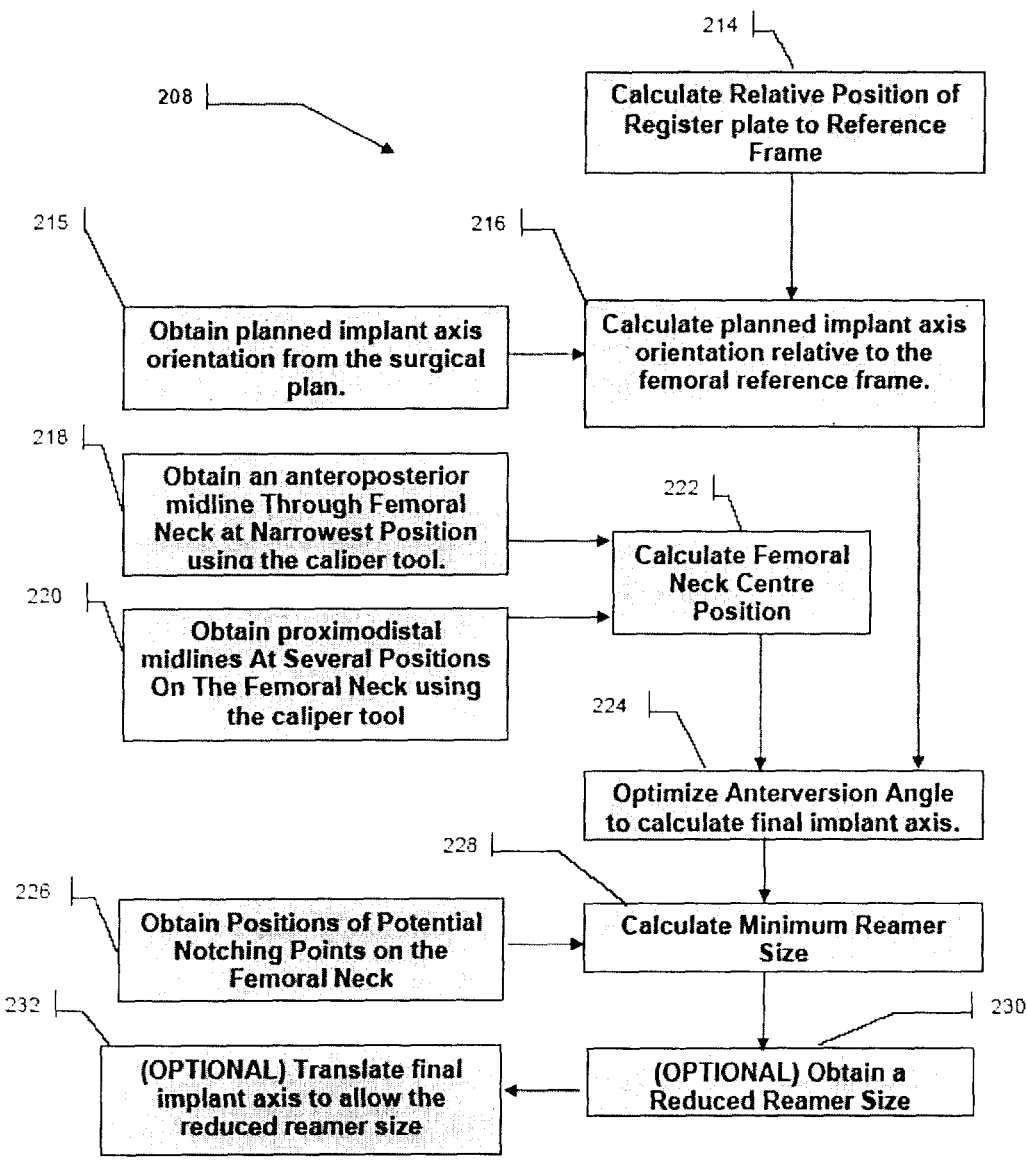
FIG. 13 shows the flowchart illustrating the method for determination of final implant axis.

With reference to FIG. 13, a general description is provided of a method 208 used to intraoperatively locate the planned implant axis 116 (shown in FIG. 1) and generate a final implant axis 180 (shown in FIG. 10) defined with respect to the femur. In step 214, the position of the registration tool 150 relative to the reference frame 146 may be recorded by taking at least one reading using the navigation system while the registration tool 150 is positioned on the femur 120 as described in FIG. 3 and FIG. 4. Using predetermined geometry and calibration of the registration tool 150, an approximate frontal plane 143 coincident with the second surface 142 and an approximate superior reference plane 141 coincident with the first surface 140 are defined relative to the femur 120 (see FIG. 14). After the single reading is taken, the registration tool 150 may be removed.

In step 215, varus/valgus angle 122 and ante/retroversion angle 138 from the preoperative surgical plans 90 and 91 are entered into the algorithm. If preoperative surgical plan 91 is not available, for example due to poor or unavailable mediolateral radiographs, ante/retroversion angle 138 may be selected based on typical anatomy, 5 degrees being a suitable value.

In step 216, using the data from steps 214 and 215, the planar geometry of the femur 120, in particular the spatial positions of the approximate superior reference plane 141 which is near coincident with superior reference plane 100, and the approximate frontal plane 143 which is near coincident with posterior reference plane 128 may be calculated and the orientation of planned implant axis 116 relative to the femur 120 may be calculated.

In step 218, a substantially anteroposterior midline 158 through the femoral neck 124 may be obtained at approximately the narrowest position on the femoral neck 124 as described in FIG. 5 and FIG. 6 by using the caliper tool 164. In step 220, a plurality of substantially proximodistal midlines 170 through the femoral neck 124 may be obtained using the caliper tool 164 as described in FIG. 7 and FIG. 8.

Figure 14:
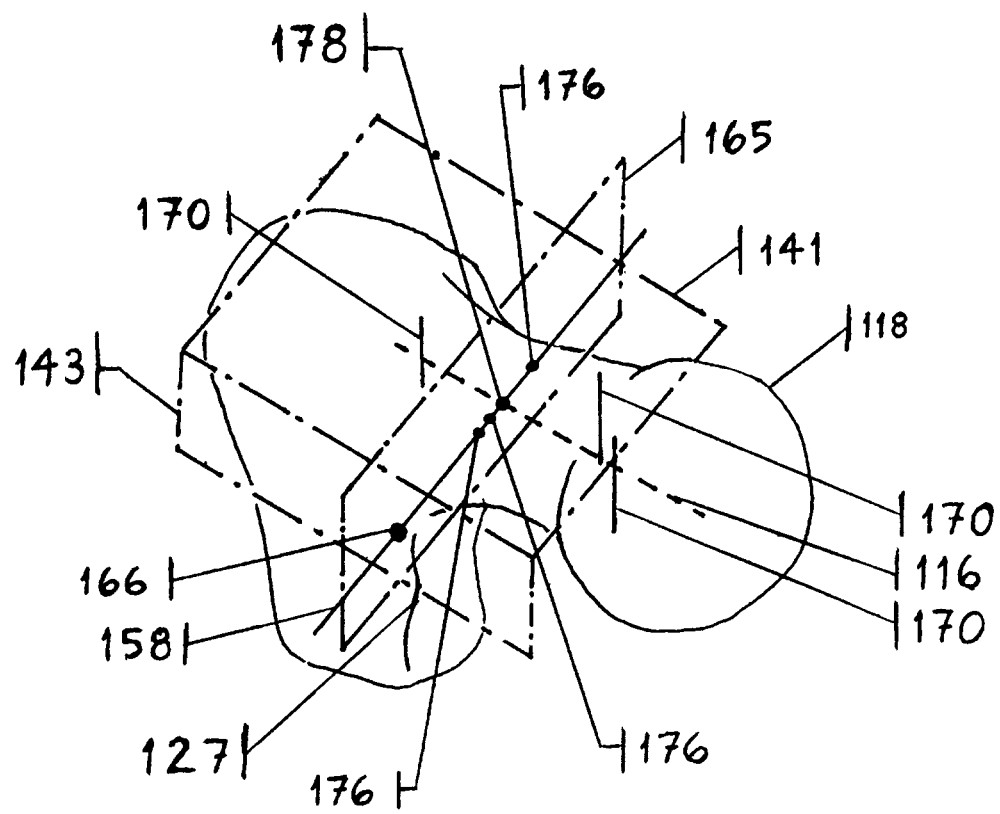
FIG. 14 illustrates the geometric determination of the femoral neck centre.

With reference to FIG. 14, step 222 of method 208 is described. The first projection plane 165 may be defined as normal to the planned implant axis 116, and passing through the intersection point 166 of the anteroposterior line 158 with the approximate frontal plane 143. The anteroposterior line 158 as obtained in step 218 and the set of proximodistal midlines 170 as obtained in step 220, which are all passing through the femoral neck 124, are projected onto the first projection plane 165 and the intersection points 176 between the anteroposterior line 158 and each of the projected proximodistal midlines 170 are calculated. A femoral neck centre 178 is the average of the intersection points 176.

Figure 15:
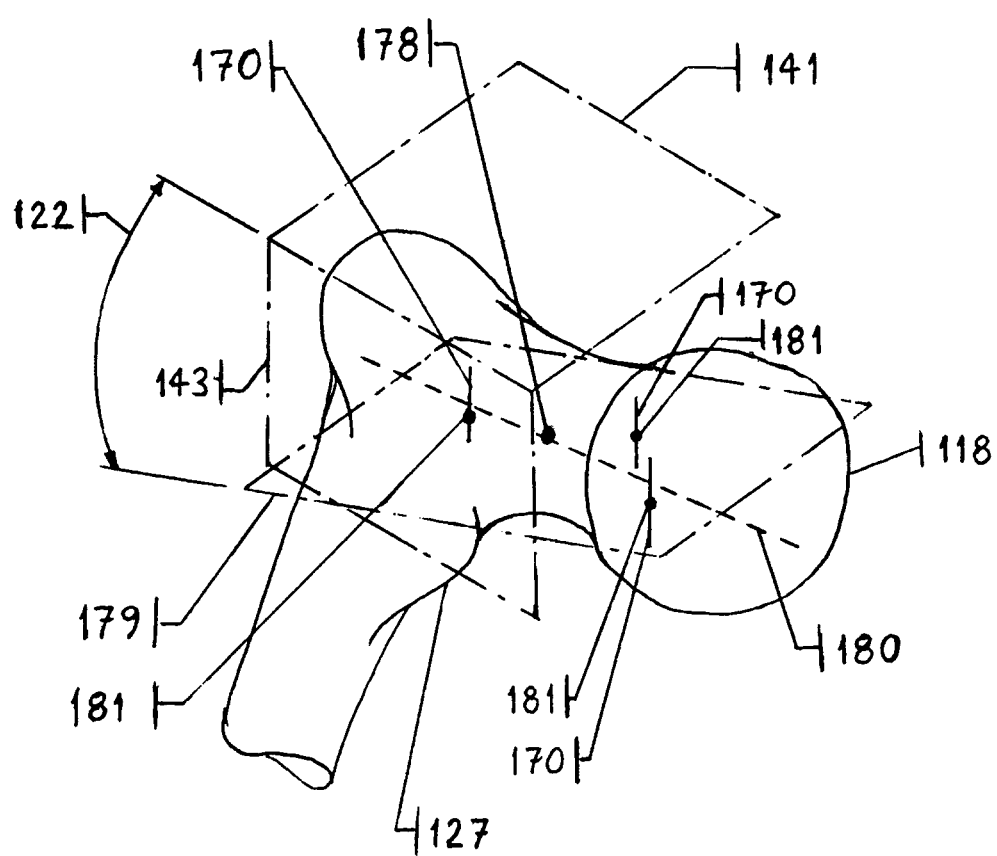
FIG. 15 illustrates the geometric determination of the final implant axis.

With reference to FIGS. 13 to 15, step 224 of method 208 is described wherein the planned implant axis 116 is optimized based on the intraoperative characterization of the femoral neck 124 provided by the proximodistal midlines 170 obtained directly from the surfaces of the femur 120 using the caliper tool 164. Step 224 corrects the planned implant axis 116 which may be inaccurate due to the typically poor quality of mediolateral radiographs. Furthermore, step 224 allows an estimated ante/retroversion angle 138 to be used and eliminates the need for a mediolateral radiograph. In step 224, using the data obtained from steps 222 and 216, a final reference plane 179 normal to the approximate frontal plane 143, rotated to the desired varus/valgus angle 122 measured relative to the approximate superior reference plane 141, and passing through the femoral neck centre 178 is calculated. Intersection points 181 are the intersections of proximodistal midlines 170 and final reference plane 179. The final implant axis 180 is the best-fitting line through intersection points 181. A suitable search algorithm for calculating final implant axis 180 is known in the art as least-squares.

Alternatively, in step steps 222 and 224, an anteverted reference plane may be defined by using an optimization technique to fit a plane to the at least 3 proximodistal midlines 170. The intersection between this anteverted reference plane and the final reference plane 179 may be calculated and used as the final implant axis 180. In this alternate embodiment femoral neck centre 178 is the intersection of anteroposterior line 158 and the anteverted reference plane, thereby eliminating the need for anteversion angle 138 and the mediolateral radiograph. Final reference plane 179 and final implant axis 180 are calculated as described in the preferred embodiment above.

With references to FIG. 9, FIG. 10, FIG. 13, FIG. 15 and FIG. 16, steps 228, 230, and 232 of method 208 are described. In step 226, the absolute spatial position of potential notching points 182 on the femoral neck 124 may be obtained by using a digitizing probe 184 as shown in FIG. 9. In step 228, using the data from step 224 and 226, calculations may be performed to obtain a minimum cylindrical radius 186 about the final implant axis 180 that will encircle potential notching points 182. This minimum cylindrical radius 186 represents the minimum femoral head reamer size that the surgeon may pass along the final implant axis 180 and describing cylindrical reamer path 188, to without cutting off bone at the potential notching points 182. In step 230, a smaller reamer size may be selected to minimize the femoral head implant size, and therefore minimize the amount of acetabular bone stock which needs to be removed to fit the corresponding acetabular implant. In step 232, and using data from step 230 and 228, a search algorithm may be used to calculate (where physically possible) the translation of the final implant axis 180 required for the specified smaller reamer to encompass the potential notching points 182. In the preferred embodiment, the orientation of the final implant axis 180 will not change in order to preserve the planned axis angles. Those skilled in the art will appreciate that by using slightly more complex search algorithms, orientation changes of final implant axis 180 within a selected range may be calculated and proposed along with or in place of axis translations to further minimize the reamer radius.

Figure 17:
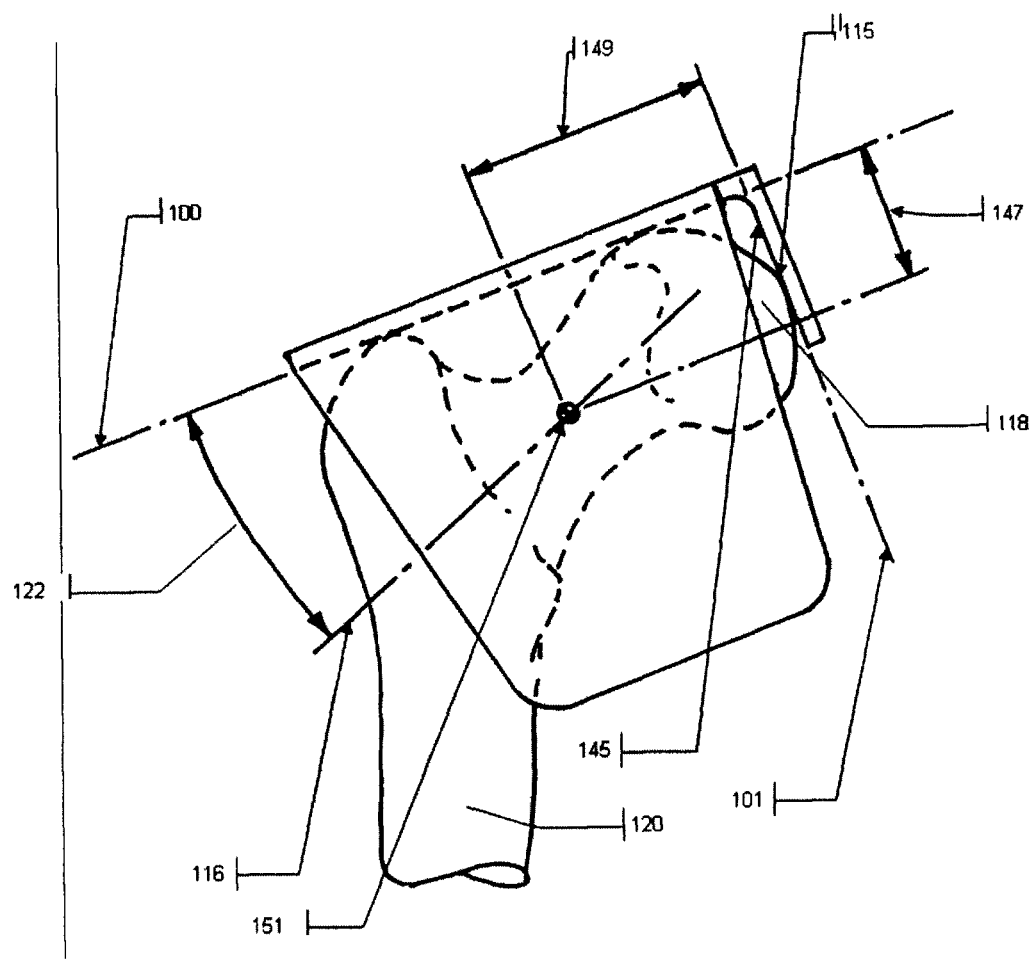
FIG. 17 illustrates an alternate embodiment of the registration tool.

Referring to FIG. 17, an alternative embodiment of the registration tool may additionally include third rigid planar surface 145 adapted to contact a sixth preselected anatomical feature of the femur such as superomedial aspect 115 of the femoral head 118. This embodiment constrains the sixth degree of freedom of the probe relative to the femur 120, allowing orientations and additionally positions of features defined in the preoperative surgical plan 90 relative to superior 100, posterior 128, and medial 101 reference planes as shown in FIG. 1, FIG. 2 and FIG. 17 to be defined relative to the femur 120 via reference frame 146 shown in FIG. 3. For example, in the alternate embodiment shown the position of planned axis 116 as projected onto the plane of the anteroposterior radiograph is defined relative to registration tool 150 by measuring dimensions 147 and 149 to point 151 on planned axis 116, thereby eliminating step 218 of FIG. 13. This alternate embodiment is generally useful when points that can be measured on the surgical planning radiographs must be located on the bone intraoperatively and cannot be conveniently located by digitizing or using a tool such as caliper tool 164.

EXAMPLES

Example 1

End-to-End Procedure

In one preferred embodiment, a surgeon utilized the apparatus and method of this invention to complete full preoperative planning, obtain required intraoperative measurements, and complete the procedure.

In this embodiment, a surgeon used an anteroposterior (AP) (FIG. 1) and mediolateral (ML) (FIG. 2) radiographs of the femur to draw the preoperative surgical plan. The radiographs were digitized and imported into a custom designed navigation system.

On the AP radiograph, a surgeon defined the superior reference plane based on a line connecting superior aspects of the femoral head and the greater trochanter (GT). A planned implant axis was also drawn the digitized radiograph and varus/valgus angle was measured between the superior reference plane and the planned implant axis. in accordance to well established practice. Superior and posterior reference planes were drawn on radiographs.

On the ML radiograph, a surgeon defined the posterior reference frame based on a "best fit" line through the posterior aspects of the femoral head, the GT, and the lesser trochanter (LT). Because the plane of the ML radiograph will usually differ from the vertical-lateral plane of the bone—it is extremely difficult to achieve perfect alignment—the posterior points may not be visible and/or may not align. With this in mind, a surgeon was able to approximate the ante/retroversion positioning of the planned implant axis on the preoperative surgical plan.

Where an ML radiograph is not available or the angle of view is such that the most posterior points of the femoral head, GT, and LT are substantially out of line, this step can be omitted and the navigation system will use a default value, a suitable value being 5 degrees of anteversion. This angle will be corrected later with intraoperative data.

It will be apparent to those skilled in the art that a variety of alternate methods may be used to plan the desired axis, for example using digital radiographs and various graphical techniques to automate the axis determination, or by using a 3 dimensional model of the patient's femur constructed from preoperative images. It is an object of the current invention to implement the planned axis accurately, and optimize the axis based on intraoperatively gathered data.

In this embodiment, a surgeon used a custom navigation system for intraoperative navigation. However, a number of commercial navigation systems are available and can be also used.

As seen in FIG. 3, a reference frame was attached to the exposed femur to allow real-time tracking of the movements of the femur by the navigation system. Examples of reference frames are known in the art and many commercial implementations are available utilizing a variety of attachment methods, attachment positions and sensor types. Examples of suitable reference frames may include models manufactured by TraxTal, Brainlab, Praxim, etc.

As seen in FIG. 3 and FIG. 4, a surgeon positioned the registration tool on the exposed femur such that first surface was in contact with the superior aspects of femoral head greater trochanter; and the second surface was in contact with the most posterior aspects of the femoral head, the greater trochanter, and the lesser trochanter. When positioned in this manner, the first and second surfaces were aligned with the first and second reference planes, respectively, and their absolute positions in space registered by the navigation system, thus defining femur geometry.

As seen in FIG. 5 and FIG. 6, a surgeon used a caliper tool to an approximate anteroposterior midline through the narrowest aspect of the femur neck. To do so, a surgeon closed the caliper faces on the superior/inferior aspects of the femoral neck at approximately the narrowest locations, and defined the line as normal to the measurement point and parallel to the caliper faces through the femoral neck.

As seen in FIG. 7 and FIG. 8, a surgeon used a caliper tool to take several (in this case 3) measurements along the femoral neck by closing the caliper faces on its anterior and posterior aspects. The measurement locations were spread out as far as possible. At each measurement location, an approximately proximodistal (PD) midline was recorded parallel to the caliper faces and through the femoral neck.

Once the caliper measurements were completed, the navigation system utilized the algorithm contained in this invention to calculate the final implant axis as closely as possible to the proposed planned implant axis and at an optimized anteversion angle. As seen in FIG. 14, the proximodistal midlines were projected onto a plane which is normal to the planned implant axis and passes through a point near the neck centre, a suitable point being the intersection of the approximate anteroposterior midline and through the narrowest aspect of the femoral neck and the plane coincident with the second surface of the register tool (i.e. passing through the most posterior aspects of the femoral head, GT, and LT). The average of the intersection positions between each of the projected PD midlines and the projected AP midline is taken as the neck centre.

The final implant axis was then calculated as the best-fitting line through the intersection points of the five PD midlines and a plane normal to the plane coincident with second surface of the register tool. (i.e., passing through the most posterior aspects of the femoral head, GT, and LT), passing through the neck centre and rotated to the proposed varus/valgus planned implant axis. The final implant axis was thereby positioned at the desired varus/valgus angle and at an anteversion angle determined by the middle of the femoral neck bone stock as measured by the caliper tool.

Figure 16:
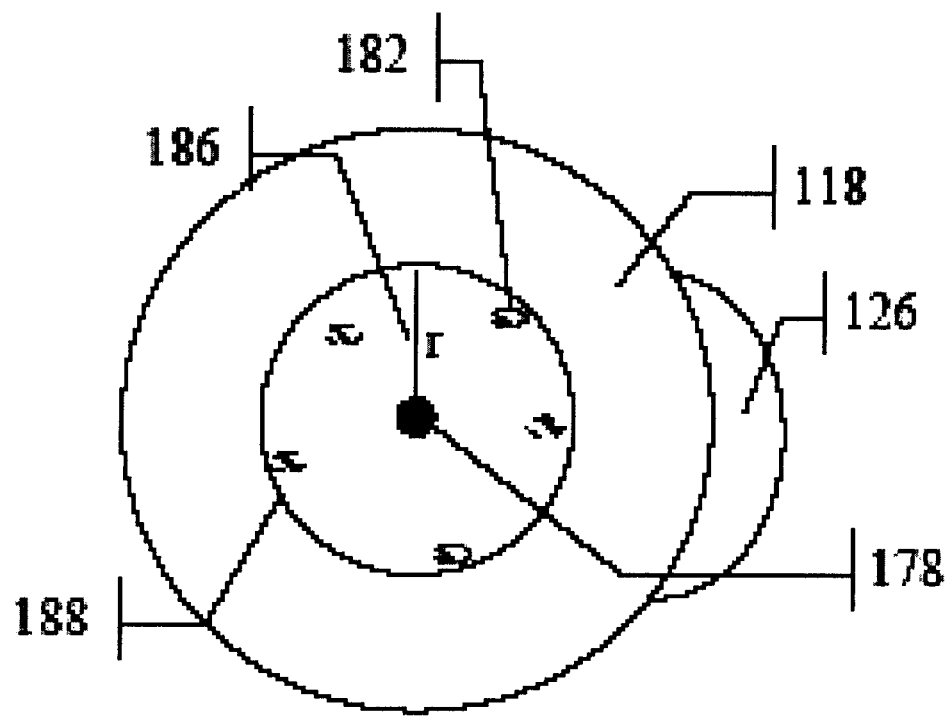
FIG. 16 illustrates the determination of minimum reamer size.

As seen in FIG. 9 and FIG. 16, to avoid notching problems, a surgeon used a conventional point digitizing probe to record potential notching points on the femoral neck. Such probes are known in the art and are usually provided as an accessory to existing surgical navigation systems such as those manufactured by Brainlab or Praxim. Once the points were obtained, the algorithm calculated the minimum cylindrical radius about the final implant axis that encircled these points and reported this radius to the surgeon. This minimum cylinder radius represents the minimum femoral head reamer size that a surgeon can pass along the final implant axis without cutting off bone at the potential notching points.

The surgeon then provided a smaller reamer size to the navigation system to try to minimize the femoral head implant size, and therefore minimize the amount of acetabular bone stock which needs to be removed to fit the corresponding acetabular implant. Using a search algorithm (several are well-known in the literature), the algorithm calculated (as was physically possible) the translation of the final implant axis required for the specified smaller reamer to pass the potential notching points. This option allowed the surgeon to accept a translation of the implant axis slightly off the middle of the femoral neck in order to use a smaller implant without notching. In the preferred embodiment, the orientation of the implant axis did not change in order to preserve the planned axis angles. Those skilled in the art will appreciate that by using slightly more complex search algorithms, orientation changes of final implant axis within a selected range may be calculated and proposed along with or in place of axis translations to further minimize the reamer radius.

On the CAS targeting screen (FIG. 11 and FIG. 12) the surgeon was able to see the position of the hand-held tracked drill guide. The tracked drill guide was adapted to be tracked by the navigation system and calibrated to report the drill axis and tip location to the algorithm. Alternately the drill itself may have been similarly adapted and calibrated, and such drills are commercially available. As the surgeon manipulated (FIG. 10) the tracked drill guide, the targeting screen distance window reported the current distance from the tracked drill guide tip to the final implant axis and the current angle between the drill axis of the tracked drill guide and the final implant axis. To minimize the amount of attention that the surgeon must pay to the targeting screen, the target symbols changed colour and an audible alarm sounded when the position and angulation of the tracked drill guide were within a predetermined tolerance range about the final implant axis.

With the tracked drill guide in position, the surgeon inserted a guide pin through the tracked drill guide and into the femur using a drill. While driving the pin, the target screen continued to provide real time feedback to the surgeon on the drill position and orientation as described above. The final orientation was recorded by tracking the TDG before removing it from the pin. With the guide pin in place, the surgeon continued with the procedure according to the specific requirements of the implant system being used.

Example 2

Cadaver and Artificial Bone Studies

An embodiment of the invention was constructed and tested on artificial bone models and cadaver bones. The latter study was performed using 5 pairs of proximal femurs in a simulated OR environment. AP and ML radiographs were taken of each bone. An expert surgeon, experienced in the operation of the mechanical device used to determine the femoral implant axis, performed the preoperative planning procedure.

Each bone had an optical tracker attached to it (FIG. 3) and each bone was registered with the CAS system built for this embodiment. The registration proceeded by using a Reference Tool (RT) described above.

On one of each pair of femurs, a novice surgeon used the CAS system to calculate a guide pin axis at the planned angles through the centre of the narrowest point of the femoral neck. The calculated target axis for the drill guide was recorded, and the final pin position measured after the novice surgeon drove the pin. The pin was moved out of the way and the expert then calculated proper position using a mechanical system currently in use. The pin was not driven in, but the targeted pin axis was recorded. On the contralateral limb, the expert surgeon used the mechanical device to calculate the proper angle and position and then drove the pin. The mechanical guide setting and the final position of the pin were measured. Following the experimental session, bones were remounted and AP/ML radiographs taken to examine the final placement.

The variabilities in deviation from the pre-operative plan in varus/valgus angles were significantly lower for our CAS method (2.0°) than the existing mechanical method (5.5°).

The mechanical/expert axis settings were significantly retroverted relative to the CAS axis (average=8°). The varus-valgus differences between the methods had low bias and were generally within 4° of one another, but differences ranged from 8° in valgus to 6.2° in varus.

The pin driving accuracy was similar for both methods and was small: typical errors were less than 2°.

REFERENCES

Amstutz H C, Beaule P E, Dorey F J, Le Duff M J, Campbell P A, Gruen T A, *Metal-on-metal hybrid surface arthroplasty: two to six-year follow-up study*, J Bone Joint Surg Am, 2004 January; 86-A(1):28-39.

Beaule P E, Amstutz H C, Le Duff M, Dorey F, *Surface arthroplasty for osteonecrosis of the hip: hemiresurfacing versus metal-on-metal hybrid resurfacing*, J Arthroplasty, 2004 December; 19(8 Suppl 3):54-8.

Callaghan J J, O'rourke M R, Saleh K J, *Why knees fail: lessons learned*, J Arthroplasty, 2004 June; 19(4 Suppl 1):31-4.

Chandler H P, Reineck F T, Wixson R L, McCarthy J C, *Total hip replacement in patients younger than thirty years old. A five-year follow-up study*, J Bone Joint Surg Am, 1981 December; 63(9):1426-34.

Daniel J, Pynsent P B, McMinn D J, *Metal-on-metal resurfacing of the hip in patients under the age of 55 years with osteoarthritis*, J Bone Joint Surg Br, 2004 March; 86(2):177-84.

Dorr L D, *Comparison of primary total hip replacements performed with a standard incision or a mini-incision*, J Bone Joint Surg Am, 2005 March; 87-A(3):675.

Duffy G P, Prpa B, Rowland C M, Berry D J, *Primary uncemented Harris-Galante acetabular components in patients 50 years old or younger: results at 10 to 12 years*, Clin Orthop Relat Res, 2004 October; (427):157-61.

Joshi A B, Porter M L, Trail I A, Hunt L P, Murphy J C, Hardinge K, *Long-term results of Charnley low-friction arthroplasty in young patients*, J Bone Joint Surg Br, 1993 July; 75(4):616-23.

McMinn D, Treacy R, Lin K, Pynsent P, *Metal on metal surface replacement of the hip. Experience of the McMinn prothesis*, Clin Orthop Relat Res, 1996 August; (329 Suppl):S89-98.

Mont M A, Rajadhyaksha A D, Hungerford D S, *Outcomes of limited femoral resurfacing arthroplasty compared with total hip arthroplasty for osteonecrosis of the femoral head*, J Arthroplasty, 2001 December; 16(8 Suppl 1):134-9.

Mont M, Bezweda H, Thomas C, Etienne G, *The results of metal on metal resurfacing hip arthroplasty: learning curve stratification of results*, American Academy of Orthopaedic Surgeons, Washington D.C., Feb. 22-27, 2005.

Shekman M, Masri B A, Greidanus N V, Garbuz D S, Duncan C P, Anglin C, Hodgson A J, Inkpen K B, *Variability of femoral positioning in hip resurfacing arthroplasty*, 51st Annual Meeting of the Orthopaedic Research Society, Washington, D.C., Feb. 20-23, 2005.

Sugano N, Nishii T, Kahahodo K, Sasama T, Sato Y, Tamura S, Sakai K T, Haraguchi K, Nishihara S, Ozono K, Yodenobu K, Yoshikawa H and Ochi T, *Combined acetabular and femoral navigation for resurfacing total hip arthroplasty*, Computer Assisted Radiology and Surgery, San Francisco, 226-230, 2000.

Treacy R B, McBryde C W, Pynsent P B, *Birmingham hip resurfacing arthroplasty. A minimum follow-up of five years*, J Bone Joint Surg Br, 2005 February; 87(2):167-70.

Wacek G and Boyle D, *Techniques of computer assisted surgery applied to metal on metal hip resurfacing procedures*, Galway-Mayo Inst. of Technology (IRL), Computer Assisted Radiology and Surgery, 2003.

Zambelli P Y, Brégand C H, Dewarrat S T, Marti G S, Baur C H and Leyvarz P F, *Planning and navigation solution in resurfacing hip surgery—A way to reduce the surgical approach*, Computer-Assisted Orthopaedic Surgery, Marbella, Spain, 2003.

While specific embodiments of the invention have been described and illustrated, such embodiments should be considered illustrative of the invention only and not as limiting the invention as construed in accordance with the accompanying specification.

All publications, patents and patent applications are herein incorporated by reference to the same extent as if each individual publication or patent application was specifically and individually indicated to be incorporated by reference.

The invention claimed is:

1. A method for locating a guide wire axis on a femoral neck, comprising:
   tracking a femur;
   registering a frame of reference with respect to the tracking of the femur from a first registration tool mounted onto the femur in a predetermined configuration;
   obtaining preoperative planned data pertaining to the femoral neck;
   digitizing femoral neck data with respect to the tracking of the femur by applying a second registration tool is against an unaltered exterior bone surface of the femoral neck at desired orientations while tracking the second registration tool, wherein said digitizing further comprises applying a first planar surface of the second registration tool against superior aspects of both the greater trochanter and the femoral head and applying a second planar surface of the second registration tool against posterior or anterior aspects of both the greater trochanter and the femoral head;
   calculating at least an orientation of the guide wire axis with respect to the tracking of the femur by associating the preoperative planned data and the femoral neck data; and
   outputting data for the orientation of the guide wire axis to guide an operator in aligning a tool with the guide wire axis.

2. The method according to claim 1, wherein the predetermined configuration has the first registration tool abutted against the femoral head, the lesser trochanter and the greater trochanter in such a way that a frontal plane of the femur is obtained as part of the frame of reference.

3. The method according to claim 2, wherein the preoperative planned data has a planned implant axis.

4. The method according to claim 3, wherein the planned implant axis is determined from an anteroposterior radiograph, and is oriented in a varus/valgus angle with respect to a superior reference plane.

5. The method according to claim 4, wherein the planned implant axis is further oriented from a mediolateral radiograph in an ante/retroversion angle.

6. The method according to claim 3, wherein the femoral neck data has an anterior posterior midline of the femoral neck, and at least two proximodistal midlines of the femoral neck.

7. The method according to claim 6, wherein the femoral neck data includes a femoral neck center calculated as an average of intersections between the anterior posterior midline and the at least two proximodistal midlines as projected on a plane normal to the planned implant axis and passing through an intersection between the anterior posterior midline and the frontal plane.

8. The method according to claim 7, wherein the guide wire axis is calculated from the preoperative planned data and the femoral neck data by defining a final reference plane normal to the frontal plane, oriented with respect to the planned implant axis, and passing through the femoral neck center, and digitizing the guide wire axis from intersection points between the at least two proximodistal midlines and the final reference plane.

9. The method according to claim 8, wherein the planned implant axis is further oriented from a mediolateral radiograph in an ante/retroversion angle.

10. The method according to claim 6, wherein the femoral neck data includes a femoral neck center calculated as an intersection between the anterior posterior midline and an anteverted reference plane defined from the at least two proximodistal midlines.

11. The method according to claim 10, wherein the guide wire axis is calculated from the preoperative planned data and the femoral neck data by defining a final reference plane normal to the frontal plane, oriented with respect to the planned implant axis, and passing through the femoral neck center, the guide wire axis being an intersection between the anteverted plane and the final reference plane.

12. The method according to claim 1, further comprising a step of registering notch points of the femoral neck with respect to the position and orientation of the femur.

13. The method according to claim 12, further comprising a step of displaying the notch points with respect to a reamer path related to the guide wire axis.

14. The method according to claim 1, wherein the femoral neck data has an anterior posterior midline of the femoral neck, and at least two proximodistal midlines of the femoral neck.

15. The method according to claim 2, wherein the predetermined configuration has a first planar surface of the first registration tool abutting a superior aspect of the femoral head and a superior aspect of the greater aspect, and a second planar surface abutting a posterior aspect of the femoral head, a posterior aspect of the greater trochanter and a posterior aspect of the lesser trochanter.

16. The method according to claim 15, wherein the predetermined configuration has a third planar surface abutting a supermedial aspect of the femoral head.

17. The method according to claim 1, wherein the steps are performed on a bone model or cadaver.

18. The method according to claim 1, wherein applying the second registration tool against the unaltered exterior bone surface comprises applying the first and the second planar surfaces against the greater trochanter and the femoral head, the planar surfaces being in a substantially perpendicular relation with one another as part of the second registration tool.

* * * * *